(12) United States Patent
Chi et al.

(10) Patent No.: US 9,550,704 B2
(45) Date of Patent: Jan. 24, 2017

(54) METHOD FOR SYNTHESIZING RADIOPHARMACEUTICALS USING A CARTRIDGE

(71) Applicant: Futurechem Co., LTD., Seoul (KR)

(72) Inventors: Dae Yoon Chi, Seoul (KR); Byoung Se Lee, Seoul (KR); Jae Hak Lee, Incheon (KR); So Young Chu, Seoul (KR); Woon Jung Jung, Seoul (KR)

(73) Assignee: FUTURECHEM CO., LTD., Seoul (KR)

( * ) Notice: Subject to any disclaimer, the term of this patent is extended or adjusted under 35 U.S.C. 154(b) by 72 days.

(21) Appl. No.: 14/401,790

(22) PCT Filed: May 24, 2013

(86) PCT No.: PCT/KR2013/004581
§ 371 (c)(1),
(2) Date: Feb. 24, 2015

(87) PCT Pub. No.: WO2013/176522
PCT Pub. Date: Nov. 28, 2013

(65) Prior Publication Data
US 2015/0232392 A1 Aug. 20, 2015

(30) Foreign Application Priority Data
May 24, 2012 (KR) .................. 10-2012-0055679

(51) Int. Cl.
| | | |
|---|---|---|
| *A61K 51/04* | (2006.01) |
| *A61K 51/08* | (2006.01) |
| *C07B 59/00* | (2006.01) |
| *C07H 5/02* | (2006.01) |
| *C07H 19/06* | (2006.01) |
| *C07D 451/02* | (2006.01) |
| *C07J 1/00* | (2006.01) |
| *C07D 233/91* | (2006.01) |
| *C07D 417/04* | (2006.01) |
| *C07C 213/08* | (2006.01) |

(52) U.S. Cl.
CPC ......... *C07B 59/007* (2013.01); *A61K 51/0453* (2013.01); *A61K 51/0455* (2013.01); *A61K 51/0491* (2013.01); *A61K 51/0493* (2013.01); *C07B 59/001* (2013.01); *C07B 59/002* (2013.01); *C07B 59/004* (2013.01); *C07B 59/005* (2013.01); *C07C 213/08* (2013.01); *C07D 233/91* (2013.01); *C07D 417/04* (2013.01); *C07D 451/02* (2013.01); *C07H 5/02* (2013.01); *C07H 19/06* (2013.01); *C07J 1/00* (2013.01)

(58) Field of Classification Search
CPC .................. A61K 51/04; A61K 51/08
See application file for complete search history.

(56) References Cited

U.S. PATENT DOCUMENTS

| | | | |
|---|---|---|---|
| 5,770,070 A * | 6/1998 | Davis .................. | G21F 9/12 210/266 |
| 6,713,042 B2 | 3/2004 | Liu | |
| 8,497,260 B2 | 7/2013 | Chi et al. | |
| 9,180,213 B2 * | 11/2015 | Engell .................. | A61K 51/082 |
| 2007/0155976 A1 | 7/2007 | Hunter et al. | |
| 2008/0305042 A1 * | 12/2008 | Gacek ................ | A61K 51/0402 424/1.89 |
| 2014/0011961 A1 | 1/2014 | Chi et al. | |

FOREIGN PATENT DOCUMENTS

| | | |
|---|---|---|
| CN | 1520315 A | 8/2004 |
| CN | 101336114 A | 12/2008 |
| JP | 2009518371 A | 5/2009 |
| KR | 10-2001-0108715 A | 12/2001 |
| KR | 10-2010-0112424 A | 10/2010 |
| KR | 10-2011-0130977 A | 12/2011 |
| KR | 10-2012-0089417 A | 8/2012 |
| WO | 99/55386 A2 | 11/1999 |
| WO | 9955386 A2 | 11/1999 |
| WO | 2007066089 A2 | 6/2007 |

OTHER PUBLICATIONS

International Search Report dated Sep. 25, 2013 for corresponding International Patent Application No. PCT/KR2013/004581, filed May 24, 2013.
Written Opinion dated Sep. 25, 2013 for corresponding International Patent Application No. PCT/KR2013/004581, filed May 24, 2013.
Office Action issued in related CN patent application No. 201380037260, dated Feb. 3, 2016.

* cited by examiner

*Primary Examiner* — Michael G Hartley
*Assistant Examiner* — Jagadishwar Samala
(74) *Attorney, Agent, or Firm* — Westman, Champlin & Koehler, P.A.; Amanda M. Prose

(57) ABSTRACT

The present invention relates to a method for synthesizing a radiopharmaceutical using a cartridge, which makes it possible to carry out several steps of reaction required for synthesizing a radiopharmaceutical in the cartridge filled with a polymer. A method for synthesizing a radiopharmaceutical according to the present invention enables each step's reaction to be carried out with the solution confined in the cartridge so as not to flow out, thus being simplified compared to the conventional methods for synthesizing radiopharmaceuticals, and expediting the synthesis thereof.

15 Claims, No Drawings

METHOD FOR SYNTHESIZING RADIOPHARMACEUTICALS USING A CARTRIDGE

TECHNICAL FIELD

The present invention relates to a method for synthesizing a radiopharmaceutical useful in the nuclear medicine field.

BACKGROUND ART

Molecular imaging is a technology in which a disease-specific image is obtained using a compound targeting a certain disease, and is applied to the diagnosis and treatment of the disease. For use in nuclear medicine imaging, radio-isotopes should emit high bio-penetration radiation that can penetrate deeply into the body and be of high sensitivity. Hence, they are useable as radiotracers which guarantee good bio-images when used even in trace amounts. Representative among nuclear medicine imaging technologies are SPECT (single photon emission computed tomography) and PET (positron emission tomography). Since these technologies are configured to employ radioisotopes with a relatively short half-life, the radiotracers should be synthesized within a short period of time. Further, when a high radiation dose is used for clinical application, the overall production procedure of radiotracers, including synthesis, purification, formulation, etc., should be performed by an automatic system in a radiation-shielded space. Fabricated on the basis of a labeling reaction in liquid phase, automatic synthesizers developed so far require both very complex synthesis processes and a long period of time for the production of radiotracers, with a low synthesis yield. There is therefore a continuous need for a method for effectively synthesizing a radiopharmaceutical.

RELATED ART DOCUMENT

Korean Patent Application Unexamined Publication No. 2012-0089417

DISCLOSURE

Technical Problem

It is an object of the present invention to provide a method for synthesizing a radiopharmaceutical, simply, at a high yield, within a short period of time.

It is another object of the present invention to provide a method for synthesizing a radiopharmaceutical by which multiple steps of chemical reactions necessary for labeling can be conducted within a single cartridge.

Technical Solution

Leading to the present invention, intensive and thorough research into the synthesis of radiopharmaceuticals, resulted in the finding that multiple steps of a synthesis procedure can be carried out within one single cartridge.

In accordance with an aspect thereof, the present invention provides a method for synthesizing a radiopharmaceutical, using a polymer-filled cartridge, comprising:

(S1) passing a radioisotope solution through a polymer-filled cartridge to trap a radioisotope;

(S2) loading reaction solution 1 to the cartridge;

(S3) labeling a precursor with the radioisotope entrapped by the cartridge in which the solution 1 is confined; and (S4) eluting the radioisotope-labeled compound from the cartridge.

In one embodiment, the synthesis method of radiopharmaceuticals may further comprise either loading reaction solution 2 for deprotection to the cartridge and deprotecting the radioisotope-labeled compound within the cartridge, or loading reaction solution 3 for conjugation to the cartridge and conjugating the radioisotope-labeled compound with a disease-targeting compound within the cartridge, prior to the elution of the radioisotope-labeled compound from the cartridge (S4).

As needed, the method may further comprise washing and drying the cartridge after each of the steps.

As used herein, the term "radioisotope" is intended to include radioisotopes useful for diagnosis and therapy of diseases in the nuclear medicine field, and the term "precursor" refers to a compound labeled with a radioisotope. The term "cartridge", as used herein, means a long cylindrical column with a hole at each terminus. The term "conjugation", as used herein means the coupling of the radioisotope-labeled compound with a disease-targeting compound.

The present invention is characterized by performing multiple steps of reactions in a single polymer-filled cartridge where the reaction solution of each step is confined. Further, in order to facilitate the reaction in each step, an effervescence phenomenon may be utilized or bubbles may be generated by aeration.

In one embodiment, the cartridge of step S1 may be filled with either:

1) a polymer; or
2) a polymer and a precursor, together.

In the case of 1), the precursor may be used in mixture with reaction solution 1.

In addition, the reaction solution 1 of step S2 may be mixed with a phase transition catalyst to promote the labeling of the precursor with the radioisotope.

The polymer useful in the present invention preferably has a structure represented by the following Chemical Formula 1-1 or 1-2:

[Chemical Formula 1-1]

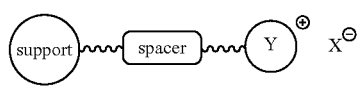

[Chemical Formula 1-2]

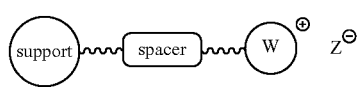

In Chemical Formulas 1-1 and 1-2,

'support' may be a non-soluble organic polymer selected from the group consisting of polystyrene, polyacrylic acid, polyacrylate, polyacrylamide, polyacrylonitrile, polyethylene glycol, polyester, polyethylene, polypropylene, polyvinylalcohol, polyethyleneimine, polymethyleneoxide, cellulose, and a combination thereof, or a non-soluble inorganic oxide selected from the group silica, aluminum oxide, titanium oxide, and zeolite, 'spacer' is a halogen-substituted or unsubstituted hydrocarbon of $C_{1-30}$ in which at least one element selected from the group consisting of nitrogen, oxygen and sulfur may be intermediated, 'Y' is a halogen-substituted or unsubstituted organic salt selected from among —NR$_1$R$_2$R$_3$ or an imidazolium salt

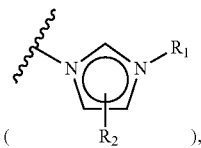

( ), a triazolium salt

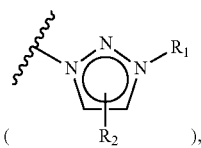

( ), a pyridinium salt

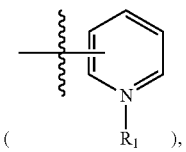

( ), a kryptopix [2,2,2]-potassium salt

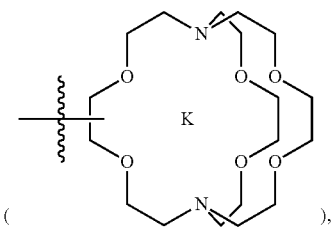

( ), and a phosphonium salt of —PR$_1$R$_2$R$_3$ wherein R$_1$, R$_2$, and R$_3$ are independently a hydrocarbon of C$_{1-30}$ in which at least one element selected from the group consisting of nitrogen, oxygen and sulfur may be intermediated, 'X' is tetrafluoroborate (BF$_4$), hexafluorophosphate (PF$_6$), hexafluoroantimony (SbF$_6$), bis(trifluoromethane)sulfone imide (N(Tf)$_2$), nitrate (NO$_3$), sodium sulfate (NaSO$_4$), potassium carbonate (KCO$_3$), bicarbonate (HCO$_3$), potassium phosphate (KHPO$_4$ or K$_2$PO$_4$), alkane carboxylate (R$_1$CO$_2$) or alkane sulfonate (R$_1$SO$_3$), wherein R$_1$ is a hydrocarbon of C$_{1-30}$ in which at least one element selected from the group consisting of nitrogen, oxygen, sulfur, phosphorous and a combination thereof may be intermediated, 'W' is phosphate (—PO$_3$), carboxylate (—CO$_2$), or sulfonate (—SO$_3$)

'Z' is hydrogen, lithium (Li), sodium (Na), potassium (K), rubidium (Rb), cesium (Cs), quaternary ammonium salt of —NR$_1$R$_2$R$_3$ or imidazolium salt

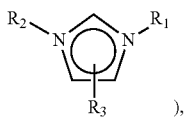

( ), triazolium salt

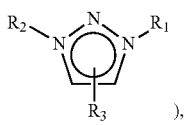

( ), or pyridinium salt

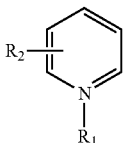

( ), or phosphonium salt of —PR$_1$R$_2$R$_3$ wherein R1, R2 and R3 are independently a hydrocarbon of C$_{2-30}$ in which at least one element selected from the group consisting of nitrogen, oxygen and sulfur may be intermediated and which may preferably have a halogen substituted or unsubstituted structure.

The precursor useful in the present invention may preferably have a structure represented by the following Chemical Formula 2-1 or 2-2:

[Chemical Formular 2-1]

2-1

[Chemical Formula 2-2]

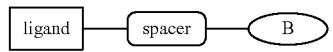

2-2 wherein,

'X' is a halogen element (F, Cl, Br, I), sulfonate (R$_1$—S(O)$_2$O—), aryl iodonium (R$_1$—I$^+$—), quaternary ammonium salt (R$_1$R$_2$R$_3$N$^+$—), hydrogen, nitro (—NO$_2$), alkoxy (R$_1$CH, triazolium salt

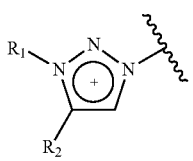

( )

or organic tin (R$_1$R$_2$R$_3$Sn—) wherein R$_1$, R$_2$ and R$_3$ are halogen-substituted or unsubstitued and independently a hydrocarbon of C$_{1-30}$ in which at least one element selected from the group consisting of nitrogen, oxygen, sulfur, phosphorus, and a combination thereof may be intermediated, 'A' is a moiety other than the radioisotope in the radiopharmaceutical compound with or without a protecting group, 'ligand' is a part made of a hydrocarbon containing at least one element selected among nitrogen, oxygen and sulfur and capable of chelation with a radioactive metal ion, 'spacer' is an oligopeptide, oligoethylene glycol, or a halogen-substituted or unsubstituted hydrocarbon of $C_{1-30}$ in which at least one selected from the group consisting of nitrogen, oxygen, sulfur, phosphorus, and a combination thereof may be intermediated, and 'B' is a biological compound selected from among an amino acid, a sugar, a lipid, and a nucleic acid, accounting for a moiety of the radiopharmaceutical compound, saving radioisotope-ligand-spacer.

Examples of Chemical Formula 2-1 of the precursors include

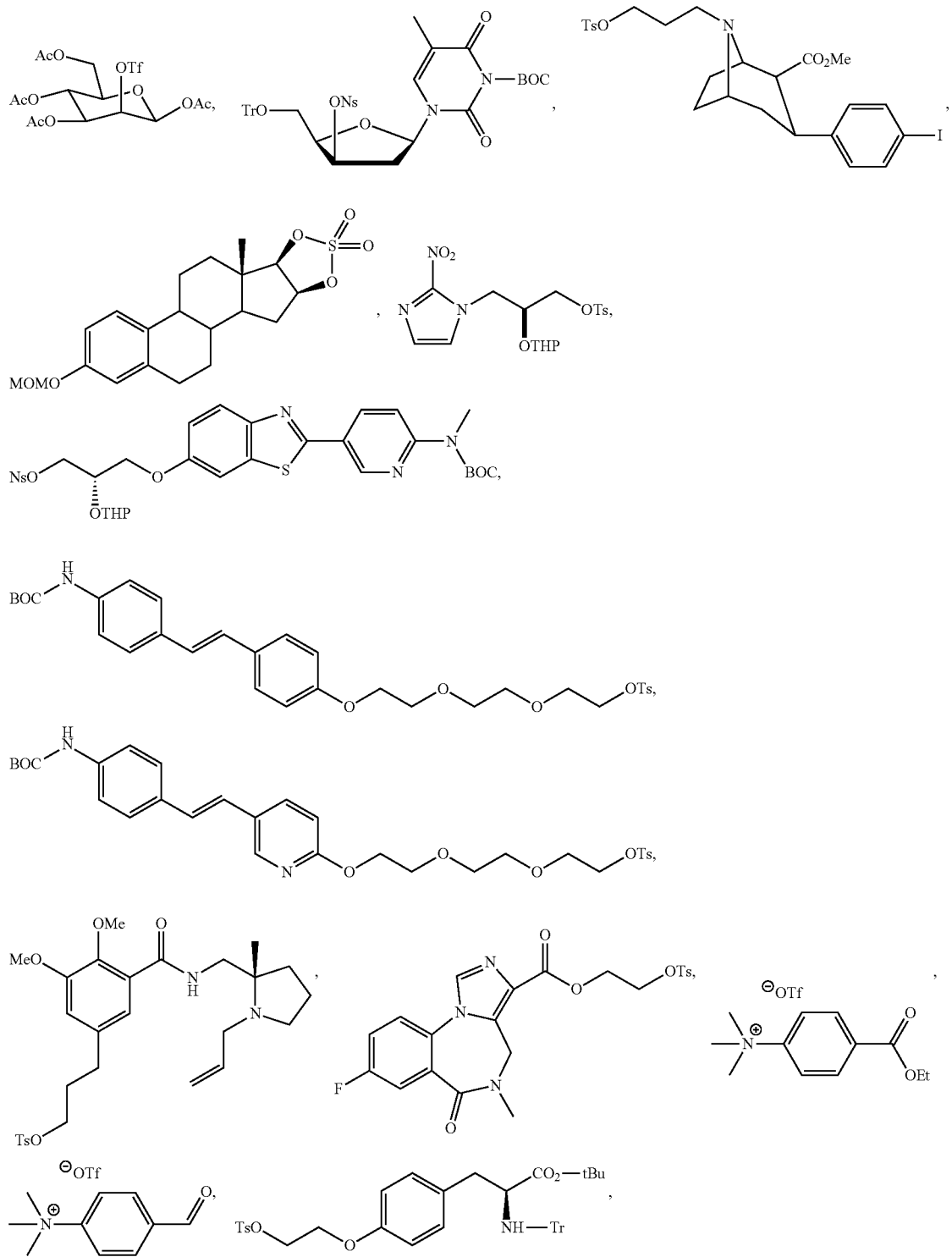

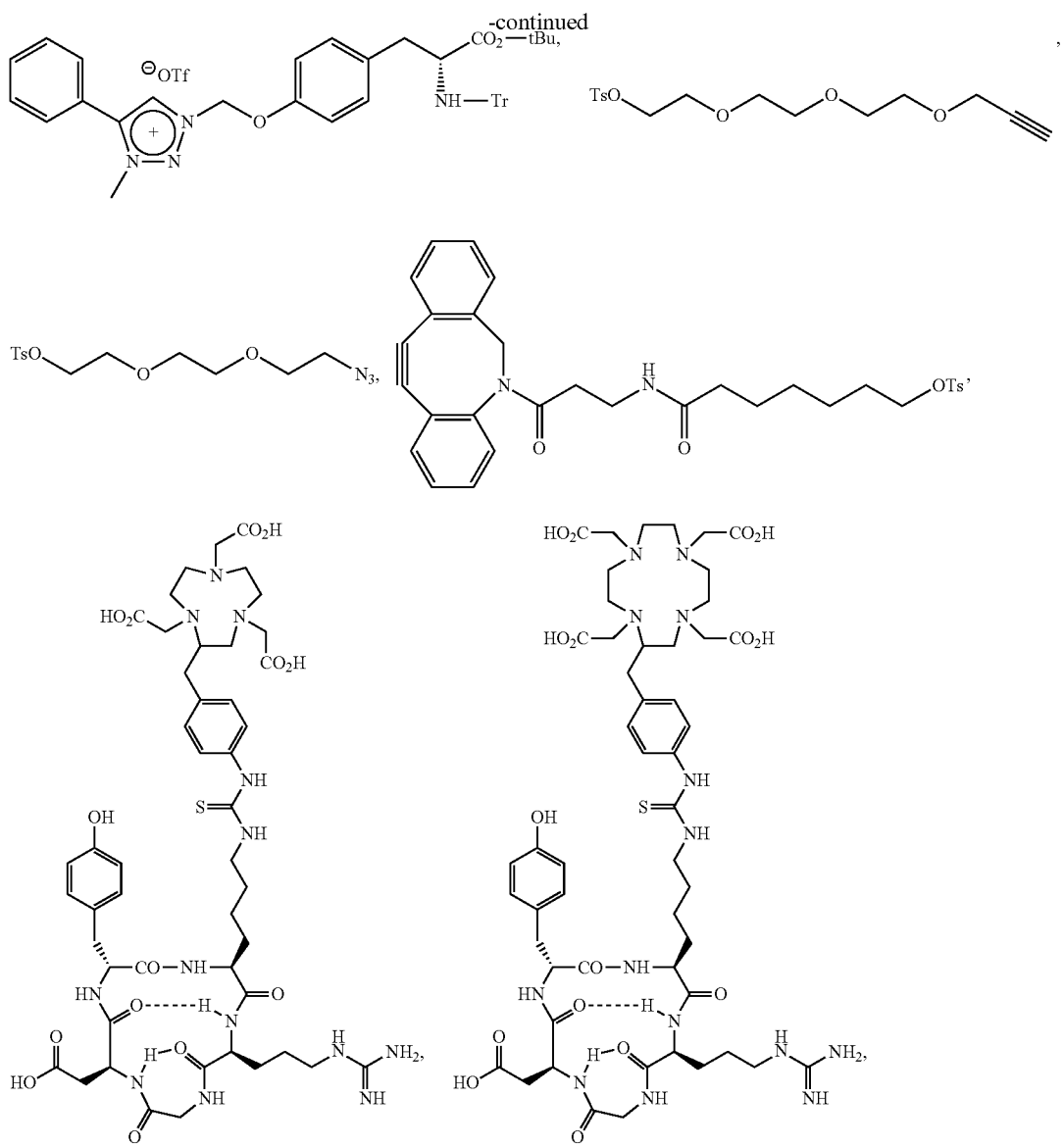
-continued
but are not limited thereto,
wherein, —OTf stands for —OS(O)$_2$—CF$_3$, —ONs for —OS(O)$_2$—C$_6$H$_4$-p-NO$_2$, -Tr for —C(Ph)$_3$, —BOC for —C(O)O-tBu, MOM for —CH$_2$OCH$_3$, -THP for -tetrahydropyranyl, and —OTs for —OS(O)$_2$—C$_6$H$_4$-p-CH$_3$.
Examples of the ligand of Chemical Formula 2-2 include
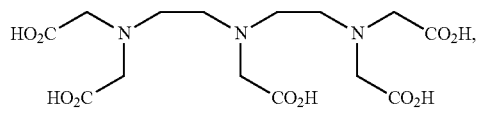
DTPA
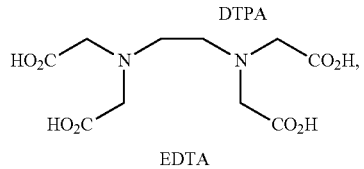
EDTA
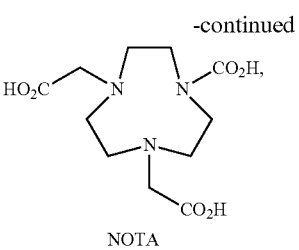
NOTA
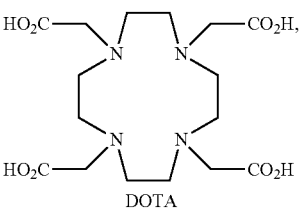
DOTA

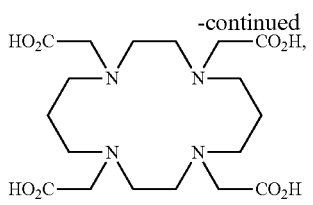

TETA

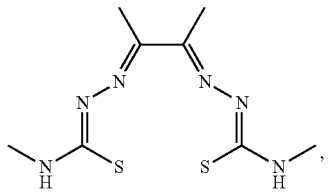

ASTM

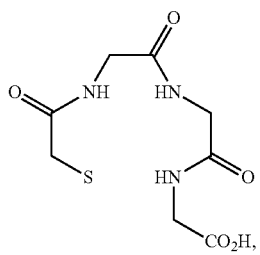

MAG3 diethylenetriamine pentaacetic acid (DTPA), ethylenediamine tetraacetic acid (EDTA), 1,4,7-triazacyclononane-N,N',N"-triacetic acid (NOTA), 1,4,7,10-tetraazacyclododecane-N,N',N",N'"-tetraacetic acid (DOTA), 1,4,8,11-tetraazacyclotetradodecane-N,N',N",N'"-tetraacetic acid (TETA), bis(thiosemicarbazone) (ATSM), and mercaptoacetyltriglycine (MAG3), but are not limited thereto.

The precursor may be introduced, together with the polymer, into the cartridge, in advance or may be loaded in mixture with reaction solution 1 to the cartridge. In this regard, the precursor and the polymer may individually weigh or may be coupled to give a polymer-precursor mixture, ahead of introduction to the cartridge. Here, the symbol "—" used in the expression polymer-precursor does not mean a covalent bond, but denotes coupling (absorption) attributed to ionic bonds or interaction between molecules or materials. The polymer-precursor mixture may be prepared by mixing the polymer represented by Chemical Formula 1-1 or 1-2 with the precursor compound represented by Chemical Formula 2-1 or 2-2 in an organic solvent, water, or a mixture thereof, removing the solvent in a vacuum, filtering the residue, and drying the filtrate.

The reaction solution 1 is a solution that may contain either the precursor or the phase transition catalyst, or both, or neither and which has a solvent selected from the group consisting of acetonitrile, tetrahydrofuran, 1,4-dioxane, diethylether, 1,2-methoxyethane, chloroform, 1,2-dichloroethane, 1,1-dichloroethane, dichloromethane, benzene, toluene, xylene, mesitylene, chlorobenzene, dichlorobenzene, acetone, methylethylketone, nitromethane, dimethylformamide, dimethylacetamide, dimethylsulfoxide, sulfolane, 1,3-dimethyl-2-imidazolidinone, triethylamine, diisopropylethylamine, pyridine, picoline, collidine, methanol, ethanol, n-propanol, n-butanol, amylalcohol, n-hexylalcohol, n-heptanol, n-octanol, isopropanol, isobutanol, iso-amylalcohol, 3-pentanol, t-butanol, t-amylalcohol, 2,3-dimethyl-2-butanol, 2-(trifluoromethyl)-2-propanol, 3-methyl-3-pentanol, 3-ethyl-3-pentanol, 2-methyl-2-pentanol, 2,3-dimethyl-3-pentanol, 2,4-dimethyl-2-pentanol, 2-methyl-2-hexanol, 2-cyclopropyl-2-propanol, 2-cyclopropyl-2-butanol, 2-cyclopropyl-3-methyl-2-butanol, 1-methylcyclopentanol, 1-ethylcyclopentanol, 3-propylcyclopentanol, 1-methylcyclohexanol, 1-ethylcyclohexanol, 1-methylcycloheptanol, and oligoethylene glycol represented by $R_1$—$(OCH_2CH_2)_n$—$OR_2$ wherein $R_1$ and $R_2$ are independently a halogen-substituted or unsubstituted hydrocarbon of $C_{1-30}$ in which at least one element selected from the group consisting of nitrogen, oxygen, sulfur, and phosphorus, and a combination thereof may be intermediated, and n is 1-3000.

Alternatively, the solution may be ionic liquid of

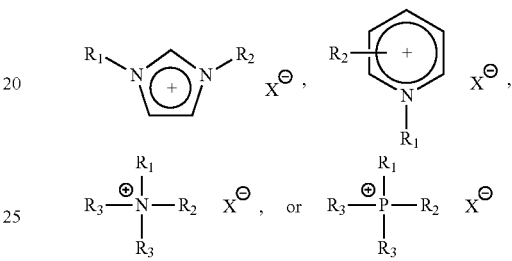

[wherein $R_1$, $R_2$, $R_3$, and $R_4$ are independently a halogen-substituted or unsubstituted hydrocarbon of $C_{1-30}$ in which at least one element selected from the group consisting of nitrogen, oxygen, sulfur, phosphorus and a combination thereof may be intermediated, X is fluoride, chloride, bromide, iodide, methanesulfonate, trifluoromethane sulfonate, hexafluorophosphate, hexafluoroantimonate, tetrafluoroborate, paratoluenesulfonate, bis(trifluorosulfonyl)imide], water, or a combination thereof.

The phase transition catalyst available in reaction solution 1 may be as follows:

A kryptopix compound, such as kryptopix[2.2.2] (4,7,13,16,21,24-hexaoxa-1,10-diazabicyclo[8.8.8]hexacosane); 4,7,13,16,21-pentaoxa-1,10-diazabicyclo[8.8.5]tricosane; 4,7,13,18-tetraoxa-1,10-diazabicyclo[8.5.5]eicosane; 5,6-benzo-4,7,13,16,21,24-hexaoxa-1,10-diazabicyclo[8.8.8]hexacos-5-ene;

A crown ether compound such as 4'-aminobenzo-15-crown-5; 4'-aminobenzo-15-crown-5; 4'-aminobenzo-15-crown-5 hydrochloride; 4'aminobenzo-18-crown-6; 4'-aminodibenzo-18-crown-6; 2-aminomethyl-15-crown-5; 2-aminomethyl-15-crown-5; 2-aminomethyl-18-crown-6; 4'-amino-5'-nitrobenzo-15-crown-5; 4'-amino-5'-nitrobenzo-15-crown-5; 1-aza-12-crown-4; 1-aza-15-crown-5; 1-aza-15-crown-5; 1-aza-18-crown-6; 1-aza-18-crown-6; benzo-12-crown-4; 5,6-benzo-4,7,13,16,21,24-hexaoxa-1,10-diazabicylclo[8.8.8]hexacos-5-ene; 1-benzyl-1-aza-12-crown-4; bis[(benzo-15-crown-5)-15-ylmethyl]pimelate; 4'-bromobenzo-15-crown-5; 4-tert-butylbenzo-15-crown-5; 4-tert-butylcyclohexano-15-crown-5; 4'carboxybenzo-15-crown-5' polyethylene glycols, and crown ether compound of polyethylene oxides; and $R_1$—$(OCH_2CH_2)_n$—$OR_2$ oligoethylene glycol wherein $R_1$ and $R_2$ are independently a halogen-substituted or unsubstituted hydrocarbon of $C_{1-30}$ in which at least one element selected from the group consisting of nitrogen, oxygen, sulfur, phosphorus, and a combination thereof may be intermediated, and n is 1-3000.

Also following compounds may be used as the phase transition catalyst:

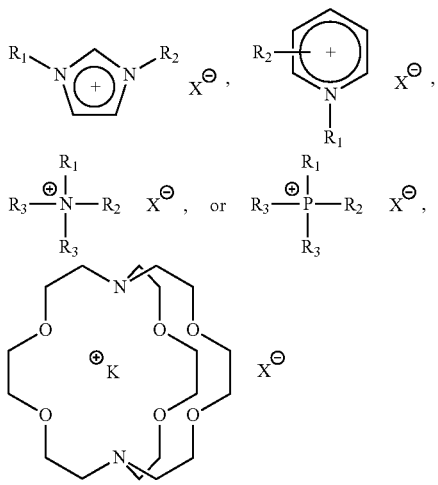

wherein $R_1, R_2, R_3$, and $R_4$ are independently a halogen-substituted or unsubstituted hydrocarbon of $C_{1-30}$ in which at least one element selected from the group consisting of nitrogen, oxygen, sulfur, phosphorus, and a combination thereof may be intermediated, X is fluoride, chloride, bromide, iodide, methanesulfonate, trifluoromethanesulfonate, hexafluorophosphate, hexafluoroantimonate, tetrafluoroborate, paratoluenesulfonate, bis(trifluorosulfonyl)imide, nitrate ($NO_3$), sodium sulfate ($NaSO_4$), potassium carbonate ($KCO_3$), bicarbonate ($HCO_3$), potassium phosphate ($KHPO_4$ or $K_2PO_4$), or acetate (OAc).

So long as it is used in the nuclear medicine, any radioisotope is available in the present invention. Inter alia, selection may be made of any one of F-18, Sc-44, Ti-45, Fe-52, Co-55, Cu-61, Cu-62, Cu-64, Ga-66, Ga-67, Cu-67, Ga-68, Br-77, Sr-83, Y-86, Zr-89, Y-90, Tc-99m, In-110, In-111, I-123, I-124, I-125, I-131, Lu-177, and Re-188.

Ahead of the step (S4), the method of the present invention may further comprise:

(S5) loading reaction solution for deprotection to the cartridge; and (S6) deprotecting the radioisotope-labeled compound in the cartridge within which the reaction solution 2 is confined.

The reaction solution 2 contains an acid or a base:

Here, the acid may be hydrochloric acid, bromic acid, iodic acid, sulfuric acid, phosphoric acid, acetic acid, benzoic acid, dichloroacetic acid, trichloroacetic acid, trifluoroacetic acid, methanesulfonic acid, trifluoromethanesulfonic acid, benzenesulfonic acid, or p-toluenesulfonic acid;

the base may be trimethylamine, triethylamine, diisopropylethylamine, 4-(N,N-dimethylamino)pyridine, 1,8-diazabicyclo[5.4.0]undec-7-ene (DBU), 1,5-diazabicyclo[4.3.0]non-5-ene (DBN), 1,4-diazabicyclo[2.2.2]octane (Dabco), N-methylmorpholine, pyridine, picoline, collidine, guanidine, 1,1,3,3-tetramethylguanidine, MOH, M'(OH)$_2$, MHCO$_3$, M$_2$CO$_3$, M'CO$_3$, M$_3$PO$_4$, M$_2$HPO$_4$, or MOR wherein M is selected from the group consisting of Li, Na, K, Cs, NH$_4$, NMe$_4$, NEt$_4$, NBu$_4$, and NMe$_3$Bn, M' is selected from the group consisting of Mg, Ca, and Ba, and R is selected from the group consisting of methyl, ethyl, isopropyl, and t-butyl.

The solvent useful in the reaction solution 2 may be selected from the group consisting of acetonitrile, tetrahydrofuran, 1,4-dioxane, diethylether, 1,2-methoxyethane, chloroform, 1,2-dichloroethane, 1,1-dichloroethane, dichloromethane, benzene, toluene, xylene, mesitylene, chlorobenzene, dichlorobenzene, acetone, methylethylketone, nitromethane, dimethylformamide, dimethylacetamide, dimethylsulfoxide, sulfolane, 1,3-dimethyl-2-imidazolidinone, triethylamine, diisopropylethylamine, pyridine, picoline, collidine, methanol, ethanol, n-propanol, n-butanol, amylalcohol, n-hexylalcohol, n-heptanol, n-octanol, isopropanol, isobutanol, isoamylalcohol, 3-pentanol, t-butanol, t-amylalcohol, 2,3-dimethyl-2-butanol, 2-(trifluoromethyl)-2-propanol, 3-methyl-3-pentanol, 3-ethyl-3-pentanol, 2-methyl-2-pentanol, 2,3-dimethyl-3-pentanol, 2,4-dimethyl-2-pentanol, 2-methyl-2-hexanol, 2-cyclopropyl-2-propanol, 2-cyclopropyl-2-butanol, 2-cyclopropyl-3-methyl-2-butanol, 1-methylcyclopentanol, 1-ethylcyclopentanol, 3-propylcyclopentanol, 1-methylcyclohexanol, 1-ethylcyclohexanol, 1-methylcycloheptanol, and oligoethylene glycol of $R_1$—(OCH$_2$CH$_2$)$_n$—OR$_2$ [wherein $R_1$ and $R_2$ are independently a halogen-substituted or unsubstituted hydrocarbon of $C_{1-30}$ in which at least one element selected from the group consisting of nitrogen, oxygen, sulfur, phosphorus, and a combination thereof may be intermediated, and n is 1-3000.

Alternatively, the solvent may be ionic liquid of

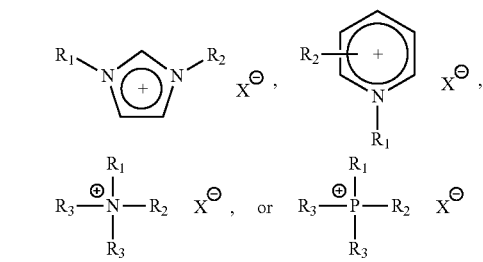

water, or a combination thereof wherein $R_1, R_2, R_3$, and $R_4$ are independently a halogen-substituted or unsubstituted hydrocarbon of $C_{1-30}$ in which at least one element selected from the group consisting of nitrogen, oxygen, sulfur, phosphorus, and a combination thereof may be intermediated, and X is fluoride, chloride, bromide, iodide, methanesulfonate, trifluoromethane sulfonate, hexafluorophosphate, hexafluoroantimonate, tetrafluoroborate, paratoluenesulfonate, bis(trifluorosulfonyl)imide.

Ahead of the step (S4), the method of the present invention may further comprise:

(S7) loading reaction solution 3 for conjugation to the cartridge; and (S8) conjugating the radioisotope-labeled compound with a disease-targeting compound in the cartridge within which the reaction solution 3 is confined.

The reaction solution 3 contains a disease-targeting compound that is capable of conjugation with the radioisotope-labeled compound.

As for the solvent, its available examples include those given for the reaction solution 2.

The radioisotope-labeled compound may preferably have a structure represented by the following Chemical Formula 3:

[Chemical Formula 3]

wherein,

'A' is a moiety other than the radioisotope in the radiopharmaceutical compound with or without a protecting group; and 'E' may be F-18, I-123, I-124, I-125, or I-131.

Examples of the radioisotope-labeled compound of Chemical Formula 3 include

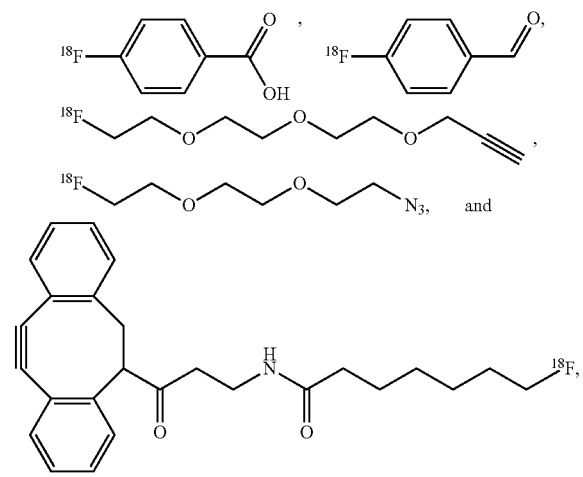

but are not limited thereto.

The disease-targeting compound preferably has a compound represented by the following Chemical Formula 4:

[Chemical Formula 4]

wherein 'T' is a biological compound selected from the group consisting of an amino acid, a sugar, a lipid, a nucleic acid, and a combination thereof, and "J" may be $NHR_1$, OH, $CO_2$—$R_1$, $N_3$, C≡C—H, $PR_1R_2$, $NHNH_2$, $ONH_2$, or

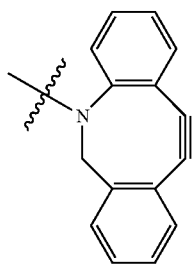

wherein $R_1$ and $R_2$ are independently a halogen-substituted or unsubstituted hydrocarbon of $C_{1-30}$ that may contain at least one element selected from the group consisting of nitrogen, oxygen, sulfur, and phosphorus.

Prior to the step S4, the method of the present invention may further comprise:

(S9) neutralizing the solution in the cartridge with an acid or a base.

Hereinafter, a method for synthesizing a radiopharmaceutical using a cartridge in accordance with the present invention will be explained in detail with reference to the accompanying drawings.

A preferred embodiment of the cartridge useful in the present invention is illustrated in FIG. 1. As shown in FIG. 1, the cartridge is preferably configured to contain a porous frit and a polymer, and has an ample space sufficiently to accommodate a reaction solution therein. FIG. 1 is an illustrative, but non-limiting example of the cartridge. For a cartridge in which an upper porous frit and a lower porous frit are placed, the polymer is located between the upper and the lower porous frit.

Next, as shown in FIG. 2, a radioisotope is entrapped within the cartridge into which a reaction solution is then introduced. Subsequently, the cartridge is locked to confine the reaction solution therein before the reaction is performed. The cartridge may be provided with a reclosable valve at a lower portion. A reaction solution is introduced upwardly from the lower portion and the cartridge is fastened with the valve to prevent leakage of the reaction solution (FIG. 2).

FIG. 3 schematically illustrates performance of chemical reactions including labeling a pharmaceutical compound with a radioisotope in the reaction solution-filled cartridge. The chemical reactions may be promoted by heating with a heater, or by providing gas or using an effervescent solvent to generate bubbles in the cartridge (FIG. 3). In these conditions, the reactants in the cartridge are well mixed so that the reactions can be facilitated.

After completion of the reactions, the radiopharmaceutical thus formed may be purified using solid phase extraction or liquid chromatography.

Advantageous Effects

The present invention pertains to the synthesis of radiopharmaceuticals using a polymer-filled cartridge. In contrast to a conventional cartridge in which [$^{18}$F]fluoride ions are entrapped before purification, the cartridge of the present invention has a space ample enough to accommodate a reaction solution therein and thus allows multiple-step reactions to be carried out therein after the entrapment of radioisotopes. The present invention does not employ the removal of solvents and water through heating distillation, which is conventionally used, and can guarantee the performance of all reaction steps in the cartridge without transferring the confined solution in or out. Hence, the method of the present invention is simpler and can synthesize radiopharmaceuticals faster than conventional methods.

DESCRIPTION OF DRAWINGS

FIG. 1 is a schematic view illustrating a structure of a cartridge useful in synthesizing a radiopharmaceutical according to the present invention.

FIG. 2 is a schematic view illustrating a procedure of filling a reaction solution, using a cartridge for synthesizing a radiopharmaceutical according to the present invention.

FIG. 3 is a schematic view illustrating a method of filling a reaction solution, using a cartridge for synthesizing a radiopharmaceutical according to the present invention.

MODE FOR INVENTION

A better understanding of the present invention may be obtained through the following examples which are set forth to illustrate, but are not to be construed as limiting the present invention.

I. Preparation of Polymer to be Filled in Cartridge

Example 1-1

Preparation of Triethyl Ammonium Salt-Coupled Polymer (Compound 1-1a)

Chloromethyl polystyrene (1.8 mmol/g, 10.0 g, 18.0 mmol) was placed in a reactor to which a mixture of dimethylformamide (DMF)/water (90 mL/10 mL) was then added. Subsequently, triethylamine (7.527 mL, 54.0 mmol) was introduced into the reactor. The resulting reaction mixture was well stirred at 50° C. for 3 hrs, and filtered through a Buchner funnel. The polymer filtrate was washed many times with acetone and dried in a vacuum. To the dried polymer was added an aqueous 0.2 M $NaHCO_3$ solution (50 mL) and the solution was stirred slowly for 5 min, followed by removing the solvent in a vacuum. This procedure was repeated three times more, for a total of 4 times. The polymer was washed once with distilled water and many times with acetone, and evaporated in a vacuum to the point of dryness to afford triethylammonium salt-coupled polymer 1-1a (12.15 g, 1.48 mmol/g). The synthesis procedure is illustrated in Reaction Scheme 1-1.

On an IR spectrum, strong peaks for $HCO_3$ anion (1645, 1450, 1292 $cm^{-1}$) were read.

[Reaction Scheme 1-1]

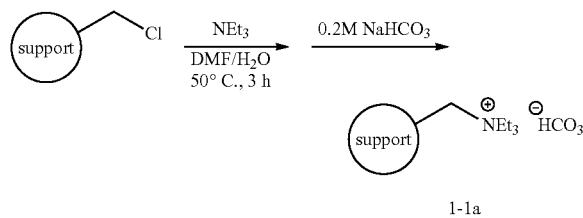

Example 1-2

Preparation of N-Methylimidazolium Salt-Coupled Polymer (Compound 1-1b)

Chloromethyl polystyrene (1.8 mmol/g, 10.0 g, 18.0 mmol) was placed in a reactor to which a mixture of dimethylformamide/water (90 mL/10 mL) was then added. Subsequently, N-methylimidazole (4.304 mL, 54.0 mmol) was introduced into the reactor. The resulting reaction mixture was well stirred at 50° C. for 3 hrs, and filtered through a Buchner funnel. The polymer filtrate was washed many times with acetone and dried in a vacuum. To the dried polymer was added an aqueous 0.2 M $NaHCO_3$ solution (50 mL) and the solution was stirred slowly for 5 min, followed by removing the solvent in a vacuum. This procedure was repeated three times more. The polymer was washed once with distilled water and many times with acetone, and evaporated in a vacuum to the point of dryness to afford N-imidazolium salt-coupled polymer 1-1b (11.82 g, 1.52 mmol/g). The synthesis procedure is illustrated in Reaction Scheme 1-2.

On an IR spectrum, strong peaks for $HCO_3$ anion (1645, 1450, 1292 $cm^{-1}$) were read.

[Reaction Scheme 1-2]

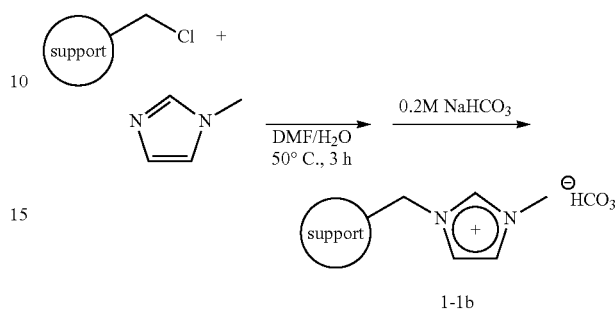

Example 1-3

Preparation of Triethylammonium Salt-Coupled Polymer (Compound 1-1c)

n-Hexyl methanesulfonate polystyrene (1.67 mmol/g, 10.0 g, 16.7 mmol) was placed in a reactor to which a mixture of acetonitrile/water (50 mL/5 mL) was then added. Subsequently, N-methylimidazole (6.65 mL, 83.5 mmol) was introduced into the reactor. The resulting reaction mixture was well stirred at 60° C. for 3 hrs, and filtered through a Buchner funnel. The polymer filtrate was washed many times with acetone and dried in a vacuum. To the dried polymer was added an aqueous 0.2 M $NaHCO_3$ solution (50 mL) and the solution was stirred slowly for 5 min, followed by removing the solvent in a vacuum. This procedure was repeated three times more. The polymer was washed once with distilled water and many times with acetone, and evaporated in a vacuum to dryness to afford triethylammonium salt-coupled polymer 1-1c (11.72 g, 1.42 mmol/g). The synthesis procedure is illustrated in Reaction Scheme 1-3.

On an IR spectrum, strong peaks for $HCO_3$ anion (1645, 1450, 1292 $cm^{-1}$) were read.

[Reaction Scheme 1-3]

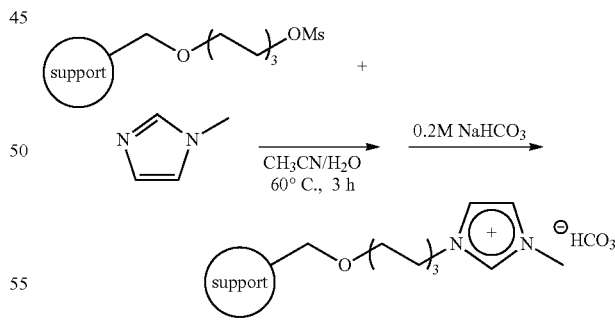

Example 1-4

Preparation of N-Methylimidazolium Salt-Coupled Polymer (Compound 1-1d)

Tetraethylene glycol monomethanesulfonate polystyrene (1.197 mmol/g, 10.0 g, 11.970 mmol) was placed in a reactor to which a mixture of acetonitrile/water (50 mL/5 mL) was then added. Subsequently, N-methylimidazole (4.77 mL, 59.85 mmol) was introduced into the reactor. The resulting reaction mixture was well stirred at 60° C. for 3 hrs, and filtered through a Buchner funnel. The polymer filtrate was washed many times with acetone and dried in a vacuum. To the dried polymer was added an aqueous 0.2 M NaHCO$_3$ solution (50 mL) and the solution was stirred slowly for 5 min, followed by removing the solvent in a vacuum. This procedure was repeated three times more. The polymer was washed once with distilled water and many times with acetone, and evaporated in a vacuum to dryness to afford N-methylimidazolium salt-coupled polymer 1-1d ((11.18 g, 1.07 mmol/g). The synthesis procedure is illustrated in Reaction Scheme 1-4.

On an IR spectrum, strong peaks for HCO$_3$ anion (1645, 1450, 1292 cm$^{-1}$) were read.

[Reaction Scheme 1-4]

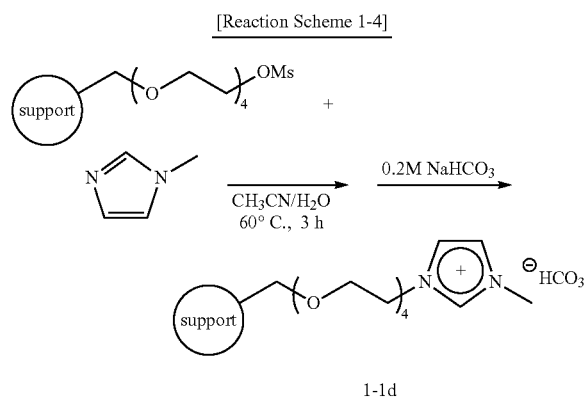

1-1d

Example 1-5

Preparation of Triphenylphosphonium Salt-Coupled Polymer (Compound 1-1e)

Chloromethyl polystyrene (1.8 mmol/g, 10.0 g, 18.0 mmol) was placed in a reactor to which a mixture of acetonitrile/water (50 mL/5 mL) was then added. Subsequently, triphenylphosphine (PPh$_3$, 14.16 g, 54.0 mmol) was introduced into the reactor. The resulting reaction mixture was well stirred at 80° C. for 24 hrs, and filtered through a Buchner funnel. The polymer filtrate was washed many times with acetone and dried in a vacuum. To the dried polymer was added an aqueous 0.2 M NaHCO$_3$ solution (50 mL) and the solution was stirred slowly for 5 min, followed by removing the solvent in a vacuum. This procedure was repeated three times more. The polymer was washed once with distilled water and many times with acetone, and evaporated in a vacuum to dryness to afford triphenylphosphonium salt-coupled polymer 1-1e (14.50 g, 1.24 mmol/g). The synthesis procedure is illustrated in Reaction Scheme 1-5.

On an IR spectrum, strong peaks for HCO$_3$ anion (1645, 1450, 1292 cm$^{-1}$) were read.

[Reaction Scheme 1-5]

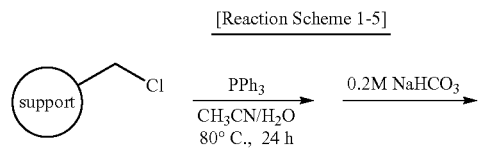

-continued

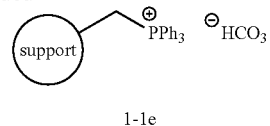

1-1e

Example 1-6

Preparation of Sulfonate Salt-Coupled Polymer (Compound 1-2a)

In a reaction vessel, chloroform (70 mL) was slowly added to polystyrene (10 g) and gently stirred at 0° C. Subsequently, ClSO$_3$H (1.00 mL, 15.0 mmol) was dropwise added to the reaction vessel, followed by gently stirring at 0° C. for one hour. After filtration through a Buchner funnel, the polymer filtrate thus obtained was washed many times with dichloromethane and dried in a vacuum. To the dried polymer was added an aqueous 0.2 M NaHCO$_3$ solution (50 mL) and the solution was stirred slowly for 5 min, followed by removing the solvent in a vacuum. This procedure was repeated three times more. The polymer was washed once with distilled water and many times with acetone, and evaporated in a vacuum to dryness to afford sulfonate salt-coupled polymer 1-2a (11.48 g, 1.31 mmol/g). The synthesis procedure is illustrated in Reaction Scheme 1-6.

On an IR spectrum, strong peaks for SO$_3$ anion (1153, 1124, 1028, 1003 cm$^{-1}$) were read.

[Reaction Scheme 1-6]

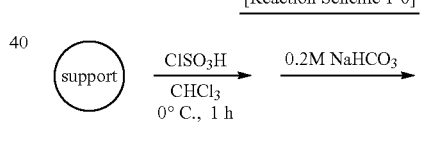

1-2a

II. Preparation of Compound to be Contained in Reaction Solution

Example 2

Preparation of Kryptopix[2.2.2]-Potassium Methanesulfonate Salt (2a)

In a round-bottom flask, kryptopix[2.2.2] (5.0 g, 13.28 mmol) and potassium methanesulfonate (KOMs, 1.78 g, 13.28 mmol) were mixed with anhydrous acetonitrile (30 mL), and reacted for 30 min at room temperature while stirring, followed by the removal of the solvent in a vacuum to afford kryptopix[2.2.2]-potassium methanesulfonate salt as a white solid (K222-KOMs, 3a, 6.78 g, 13.28 mmol). This reaction procedure is illustrated in the following Reaction Scheme 2.

[Reaction Scheme 2]

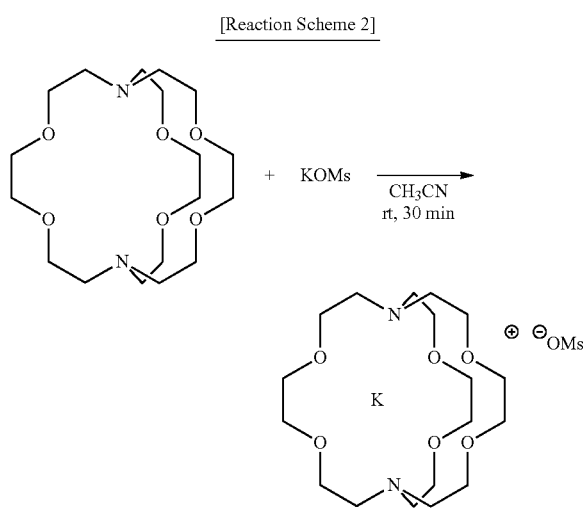

III. Preparation of Polymer-Precursor Mixture

Example 3-1

Preparation of Polymer-Precursor Mixture 3a

A polystyrene polymer (10.0 g) and a precursor compound (2-1a, 500 mg, 1.78 mmol) were introduced into a reaction vessel to which dimethylformamide (50 mL) was then slowly added. This mixture was well stirred for 10 min, slowly diluted with water (100 mL) and well stirred for 30 min at room temperature. The reaction mixture was filtered, washed many times with water, and dried in a vacuum to afford a polymer-precursor mixture 3a (10.50 g, 0.17 mmol/g). The reaction procedure is illustrated in the following Reaction Scheme 3-1.

[Reaction Scheme 3-1]

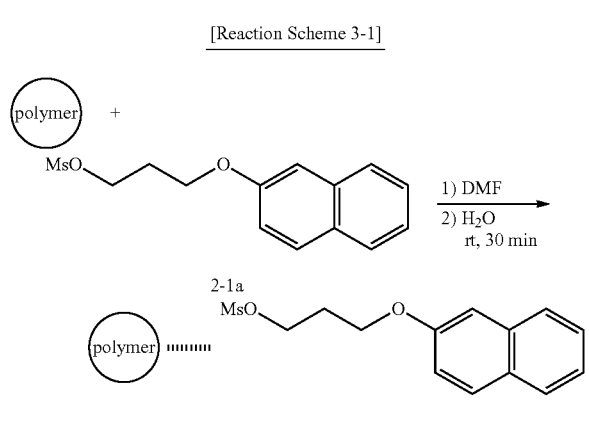

Example 3-2

Preparation of Polymer-Precursor Mixture 3b

A C-18 silica gel polymer (10.0 g) and a precursor compound (2-1a, 500 mg, 1.78 mmol) were introduced into a reaction vessel to which CH$_3$CN (50 mL) was then slowly added. This mixture was well stirred for 10 min, slowly diluted with water (100 mL) and well stirred for 30 min at room temperature. The reaction mixture was filtered, washed many times with water, and dried in a vacuum to afford a polymer-precursor mixture 3b (10.50 g, 0.17 mmol/g). The reaction procedure is illustrated in the following Reaction Scheme 3-2.

[Reaction Scheme 3-2]

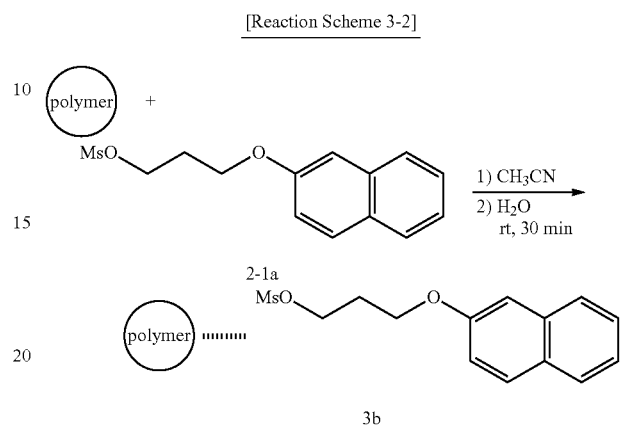

Example 3-3

Preparation of Polymer-Precursor Mixture 3c

The triethylammonium salt-coupled polymer (1-1a, 10.0 g) obtained in Example 1-1 and a precursor compound (2-1a, 500 mg, 1.78 mmol) were introduced into a reaction vessel to which CH$_3$CN (50 mL) was slowly added. This mixture was well stirred for 10 min, slowly diluted with water (100 mL) and well stirred for 30 min at room temperature. The reaction mixture was filtered, washed many times with water, and dried in a vacuum to afford a polymer-precursor mixture 3c (10.50 g, 0.17 mmol/g). The reaction procedure is illustrated in the following Reaction Scheme 3-3.

[Reaction Scheme 3-3]

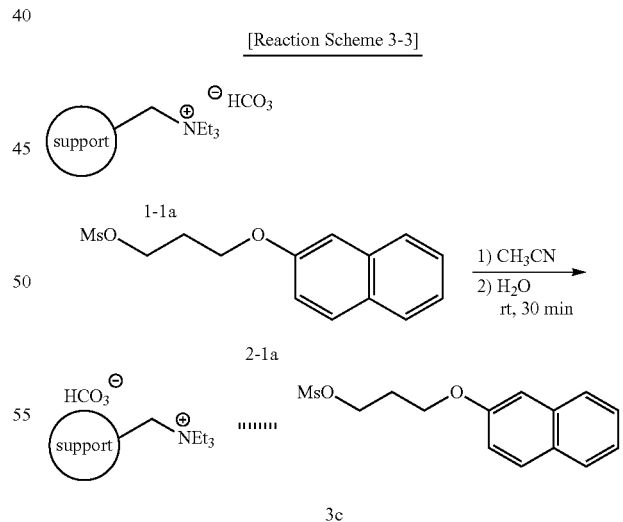

Example 3-4

Preparation of Polymer-Precursor Mixture 3d

The N-methylimidazolium salt-coupled polymer (1-1b, 10.0 g) obtained in Example 1-2 and a precursor compound (2-1a, 500 mg, 1.78 mmol) were introduced into a reaction vessel to which CH₃CN (50 mL) was then slowly added. This mixture was well stirred for 10 min, slowly diluted with water (100 mL) and well stirred for 30 min at room temperature. The reaction mixture was filtered, washed many times with water, and dried in a vacuum to afford a polymer-precursor mixture 3d (10.50 g, 0.17 mmol/g).

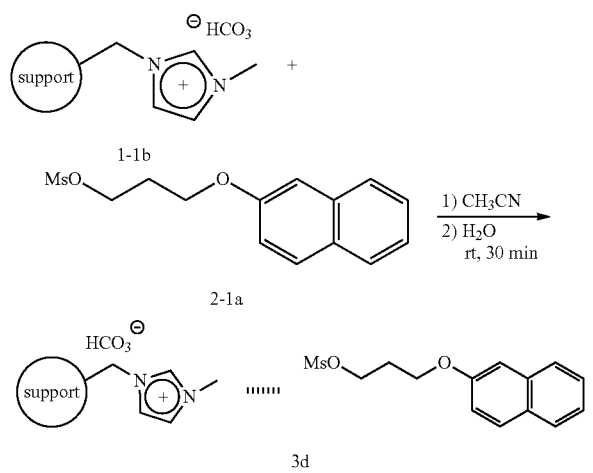

Example 3-5

Preparation of Polymer-Precursor Mixture 3D

The N-methylimidazolium salt-coupled solid support (3c, 10.0 g) obtained in Example 1-2 was introduced into a reaction vessel to which a solution of precursor compound (2a, 500 mg, 1.78 mmol) in CH₃CN (5 mL) was then slowly added. This mixture was well stirred for 10 min at room temperature, and dried in a vacuum to afford a polymer-precursor mixture 3d (10.50 g, 0.17 mmol/g).

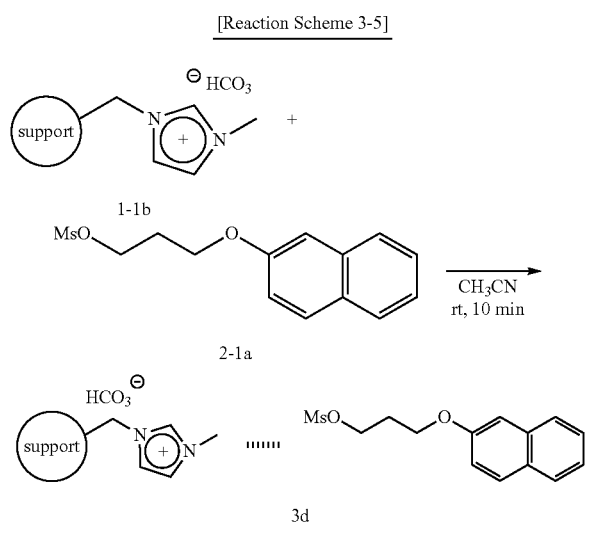

Example 3-6

Preparation of Polymer-Precursor Mixture 3e

The triethylammonium salt-coupled polymer 1-1a (50 mg) obtained in Example 1-1 and a precursor compound 2-1s (0.1 mg) were introduced into a round-bottom flask to which CH₃CN (2 mL) was then slowly added. This mixture was well stirred for 10 min at room temperature, followed by removing the solvent in a vacuum to afford a polymer-precursor mixture 3e (50 mg).

(Reaction Scheme 3-6)

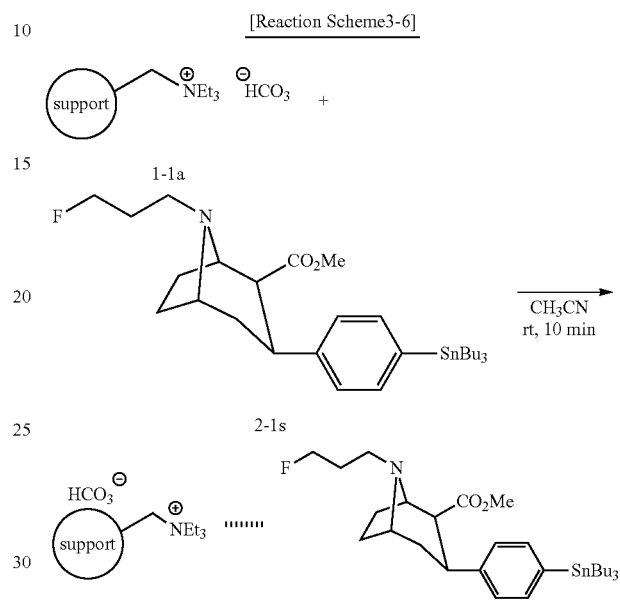

Example 3-7

Preparation of Polymer-Precursor Mixture 3f

The triethylammonium salt-coupled polymer 1-1a (50 mg) obtained in Example 1-1 and a precursor compound 2-1t (0.1 mg) were introduced into a round-bottom flask to which CH₃CN (2 mL) was then slowly added. This mixture was well stirred for 10 min at room temperature, followed by removing the solvent in a vacuum to afford a polymer-precursor mixture 3f (50 mg).

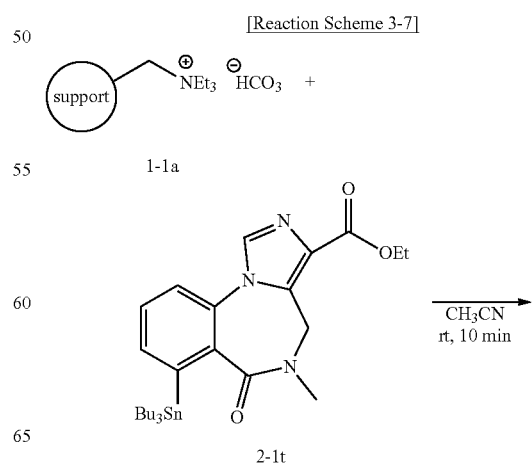

-continued

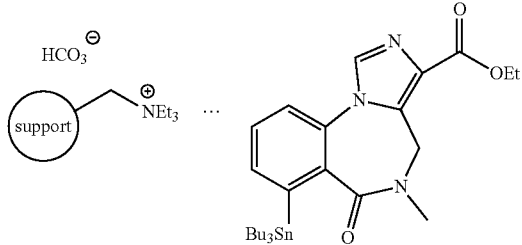

IV. F-18 Labeling Reaction

Example 4-1

F-18 Labeling of Precursor 2-1a

The polymer-precursor mixture 3c or 3d, obtained in Examples 3-3 and 3-4, respectively, was loaded in an amount of 100 mg in a cartridge. Using a syringe, 3 mL of distilled water was allowed to flow through the polymer-precursor mixture. Then, an aqueous solution of F-18 ions (3-5 mCi, 0.5 mL) was added to the mixture. After the cartridge was purged with nitrogen for 5 min, reaction solution 1 (t-amyl alcohol 0.5 mL, or t-amyl alcohol 0.5 mL in which kryptopix[2.2.2]-potassium methanesulfonate salt (3a, 10 mg) of Example 2 was dissolved) was introduced upwardly from the bottom of the cartridge which was then fastened with a valve. The cartridge was placed in a heating furnace and heated for 15 min at 120° C. After being withdrawn from the heating furnace, the cartridge was washed with acetonitrile (3 mL). The reaction procedure is illustrated in the following Reaction Scheme 4, and results are summarized in Table 1, below.

[Reaction Scheme 4]

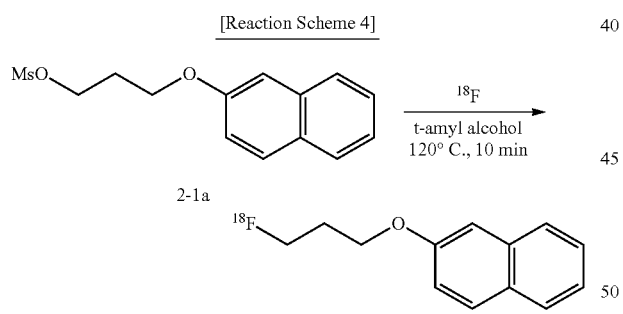

(wherein, OMs is as defined above)

TABLE 1

| | Polymer-precursor mixture | | | |
|---|---|---|---|---|
| | Example 3-3 (Compound 3c) | | Example 3-4 (Compound 3d) | |
| Reaction Solution | t-Amyl alcohol | Kryptopix[2.2.2]-potassium methanesulfonate-dissolved t-amyl alcohol | t-Amyl alcohol | Kryptopix[2.2.2]-potassium methanesulfonate-dissolved t-amyl alcohol |
| Amount left in cartridge after reaction (mCi) | 3.27 | 1.25 | 2.56 | 0.83 |

TABLE 1-continued

| | Polymer-precursor mixture | | | |
|---|---|---|---|---|
| | Example 3-3 (Compound 3c) | | Example 3-4 (Compound 3d) | |
| Acetonitrile solution after reaction (mCi) | 0.02 | 1.98 | 0.79 | 2.48 |
| Radio-TLC (%) | 0.0 | 75 | 86 | 95 |
| Radiochemical Yield (%) | 0.0 | 46.0 | 20.4 | 71.2 |

In Table 1, Radio-TLC stands for radio-thin layer chromatography, and radiochemical yield (%) is calculated according to the equation:

[Radiation dose of acetonitrile solution/(radiation dose left in cartridge+radiation dose of acetonitrile solution)]×Radio-TLC (%).

Example 4-2

F-18 Labeling of Precursor 2-1a

Together with precursor compound 2-1a (5 mg), 100 mg of each of polymers 1-1a to 1-1e, respectively obtained in Examples 1-1 to 1-5, was loaded into a cartridge. Using a syringe, 3 mL of distilled water was allowed to flow through the mixture. Then, an aqueous solution of F-18 ions (3-5 mCi, 0.5 mL) was added to the mixture. After the cartridge was purged with nitrogen for 5 min, reaction solution 1 (t-amyl alcohol 0.5 mL in which kryptopix[2.2.2]-potassium methanesulfonate salt (3a, 10 mg) of Example 2 was dissolved) was introduced upwardly from the bottom of the cartridge which was then fastened with a valve. The cartridge was placed in a heating furnace and heated for 15 min at 120° C. After being withdrawn from the heating furnace, the cartridge was washed with acetonitrile (3 mL). The reaction procedure is illustrated in the following Reaction Scheme 4-1, and results are summarized in Table 2, below.

[Reaction Scheme 4-1]

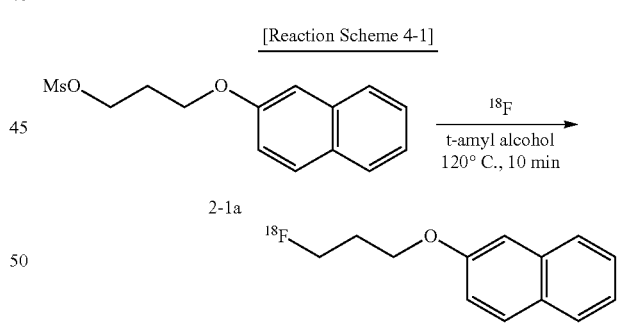

(wherein, OMs is as defined above.)

TABLE 2

| | Polymer | | | | |
|---|---|---|---|---|---|
| | 1-1a | 1-1b | 1-1c | 1-1d | 1-1e |
| Amount left in cartridge after reaction (mCi) | 1.92 | 1.66 | 1.30 | 1.12 | 1.78 |
| Acetonitrile solution after reaction (mCi) | 2.10 | 2.73 | 3.27 | 3.15 | 2.39 |
| Radio-TLC (%) | 86 | 92 | 98 | 99 | 85 |
| Radiochemical Yield (%) | 44.9 | 57.2 | 70.1 | 73.0 | 48.7 |

Example 4-3

F-18 Labeling of Precursor 2-1a

The polymers 1-1a to 1-1e, prepared in Examples 1-1 to 1-5, were loaded in an amount of 100 mg into respective cartridges. Using a syringe, 3 mL of distilled water was allowed to flow through the polymer. Then, an aqueous solution of F-18 ions (3-5 mCi, 0.5 mL) was added to the polymer. After the cartridge was purged with nitrogen for 1 min, reaction solution 1 (t-amyl alcohol 0.5 mL in which kryptopix[2.2.2]-potassium methanesulfonate salt (3a, 10 mg) of Example 2 was dissolved) was introduced upwardly from the bottom of the cartridge which was then fastened with a valve. The cartridge was placed in a heating furnace and heated for 15 min at 120° C. After being withdrawn from the heating furnace, the cartridge was washed with acetonitrile (3 mL). The reaction procedure is illustrated in the following Reaction Scheme 4-2, and results are summarized in Table 3, below.

[Reaction Scheme 4-2]

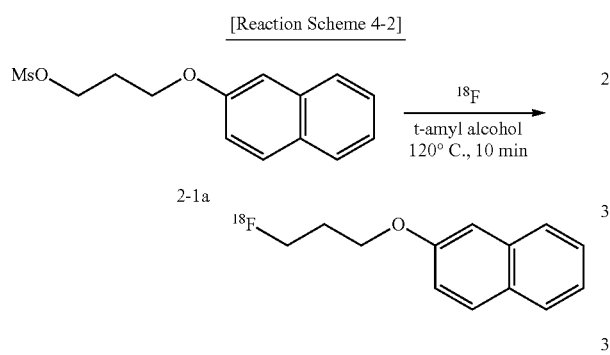

(wherein, OMs is as defined above.)

TABLE 3

|  | Polymer | | | | |
| --- | --- | --- | --- | --- | --- |
|  | 1-1a | 1-1b | 1-1c | 1-1d | 1-1e |
| Amount left in cartridge after reaction (mCi) | 1.62 | 1.69 | 1.09 | 1.12 | 1.43 |
| Acetonitrile solution after reaction (mCi) | 2.40 | 2.93 | 3.20 | 3.35 | 2.70 |
| Radio-TLC (%) | 94 | 97 | 100 | 100 | 93 |
| Radiochemical Yield (%) | 56.1 | 61.5 | 74.6 | 74.9 | 60.8 |

V. Synthesis of Representative Radiopharmaceuticals

Examples 5-1 to Example 5-23

Example 5-1

Synthesis of [$^{18}$F]FDG

The polymer 1-1d (100 mg), prepared in Example 1-4, was loaded into a cartridge. Using a syringe, 3 mL of distilled water was allowed to flow through the polymer. Then, an aqueous solution of F-18 ions (3.41 mCi, 1.0 mL) was added to the mixture. Also, acetonitrile (3 mL) was allowed to flow through the polymer using a syringe. After the cartridge was purged with nitrogen for 1 min, reaction solution 1 (acetonitrile 0.5 mL in which kryptopix[2.2.2]-potassium methanesulfonate salt (3a, 15 mg) of Example 2 was dissolved) was introduced upwardly from the bottom of the cartridge which was then fastened with a valve. The cartridge was placed in a heating furnace and heated for 10 min at 100° C., and transferred to a furnace maintained at room temperature. Then, reaction solution 2 (0.5 M NaOMe in MeOH, 0.5 mL) was introduced upwardly from the bottom of the cartridge after which nitrogen gas was also fed from the bottom slowly for 5 min. After being withdrawn from the furnace, the cartridge was allowed to drain the solution therefrom and washed with acetonitrile (3 mL) (Reaction Scheme 5-1).

A radiation dose of 0.01 mCi was detected in the empty cartridge while the released solution exhibited a radiation dose of 2.65 mCi. The radio-TLC (%) was measured at 77% (radiochemical yield (%)=77%).

[Reaction Scheme 5-1]

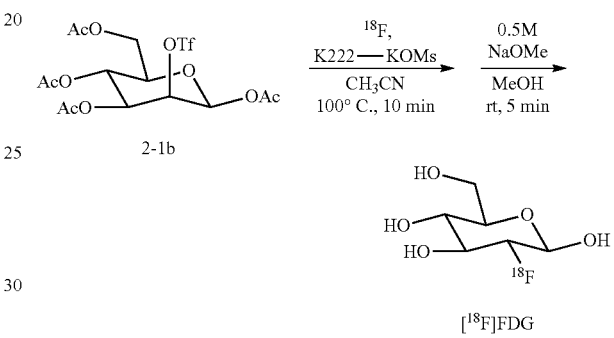

(wherein OTf is as defined above)

Example 5-2

Synthesis of [$^{18}$F] FDG

The polymer 1-1d (100 mg), prepared in Example 1-4, was loaded into a cartridge. Using a syringe, 3 mL of distilled water was allowed to flow through the polymer. Then, an aqueous solution of F-18 ions (4.65 mCi, 1.0 mL) was added to the mixture. Also, acetonitrile (3 mL) was allowed to flow through the polymer using a syringe. After the cartridge was purged with nitrogen for 1 min, reaction solution 1 (acetonitrile 0.5 mL in which kryptopix[2.2.2]-potassium methanesulfonate salt (3a, 15 mg) of Example 2 and precursor compound 2-1c (10 mg) were dissolved) was introduced upwardly from the bottom of the cartridge which was then fastened with a valve. The cartridge was heated for 10 min at 100° C. in a heating furnace, and then cooled to 120° C. Then, reaction solution 2 (2.0 N HCl in EtOH, 0.5 mL) was introduced upwardly from the bottom of the cartridge which was then fastened with a valve. Again, the cartridge was heated at 100° C. for 5 min and transferred to a furnace maintained at room temperature. Using a syringe, an aqueous 0.2 M $K_3PO_4$ solution (3 mL) was fed from the bottom. After being withdrawn from the furnace, the cartridge was allowed to drain the solution therefrom and washed with acetonitrile (3 mL) (Reaction Scheme 5-2).

A radiation dose of 0.00 mCi was detected in the empty cartridge while the released solution exhibited a radiation dose of 3.31 mCi. The radio-TLC (%) was measured at 85% (radiochemical yield (%)=85%).

[Reaction Scheme 5-2]

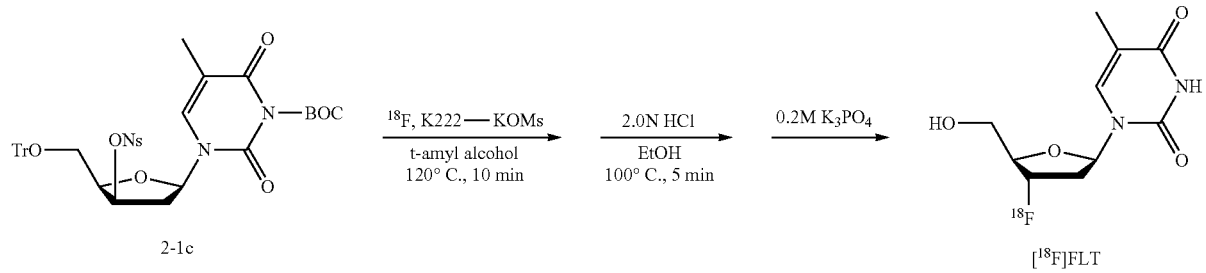

(wherein Tr, ONs, and BOC are as defined above, respectively)

Example 5-3

Synthesis of [18F]FP-CIT

The polymer 1-1d (100 mg), prepared in Example 1-4, was loaded into a cartridge. Using a syringe, 3 mL of distilled water was allowed to flow through the polymer. Then, an aqueous solution of F-18 ions (3.83 mCi, 1.0 mL) was added to the mixture. Also, acetonitrile (3 mL) was allowed to flow through the polymer using a syringe. After the cartridge was purged with nitrogen for 1 min, reaction solution 1 (t-amylalcohol 0.5 mL in which kryptopix[2.2.2]-potassium methanesulfonate salt (3a, 15 mg) of Example 2 was dissolved) was introduced upwardly from the bottom of the cartridge which was then fastened with a valve. The cartridge was heated for 10 min at 120° C. in a heating furnace, withdrawn from the furnace, and then washed with acetonitrile (3 mL) (Reaction Scheme 5-3).

A radiation dose of 1.35 mCi was detected in the empty cartridge while the released solution exhibited a radiation dose of 1.48 mCi. The radio-TLC (%) was measured at 87% (radiochemical yield (%)=45.5%).

[Reaction Scheme 5-3]

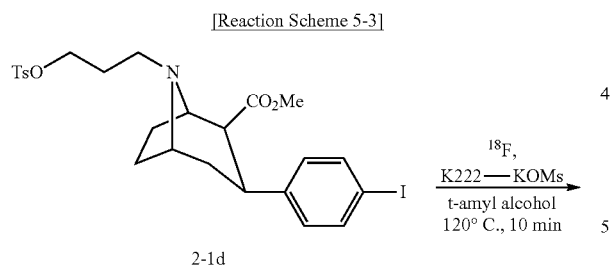

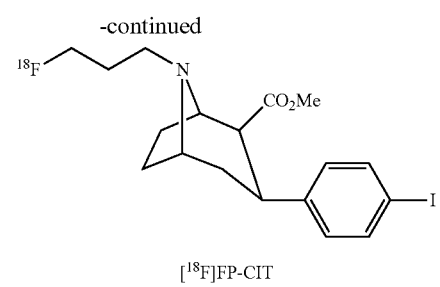

(wherein TsO is as defined above).

Example 5-4

Synthesis of [$^{18}$F]FES

[$^{18}$F]FES was synthesized in the same manner as in Example 5-2, with the exception that precursor 2-1e (5 mg) was used (Reaction Scheme 5-4).

A radiation dose of 0.02 mCi was detected in the empty cartridge while the released solution exhibited a radiation dose of 3.45 mCi. The radio-TLC (%) was measured at 76% (radiochemical yield (%)=75.6%).

[Reaction Scheme 5-4]

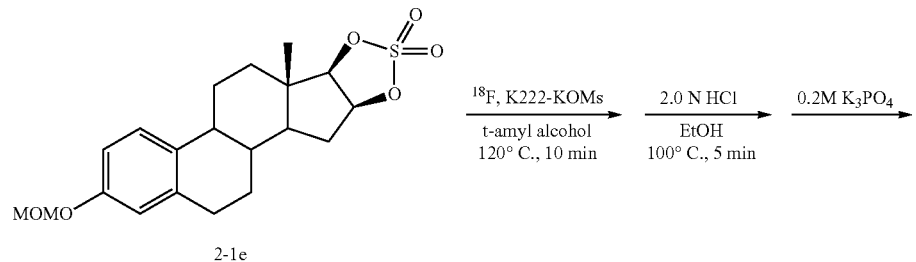

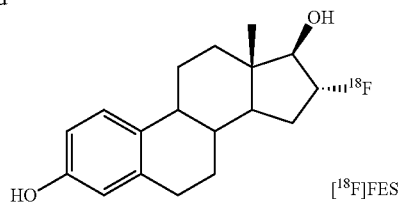

(wherein MOM is as defined above)

Example 5-5

Synthesis of [$^{18}$F]FMISO

[$^{18}$F] FMISO was synthesized in the same manner as in Example 5-2, with the exception that precursor 2-1f (5 mg) was used (Reaction Scheme 5-4). A radiation dose of 0.01 mCi was detected in the empty cartridge while the released solution exhibited a radiation dose of 3.11 mCi. The radio-TLC (%) was measured at 56% (radiochemical yield (%)=55.8%).

[Reaction Scheme 5-5]

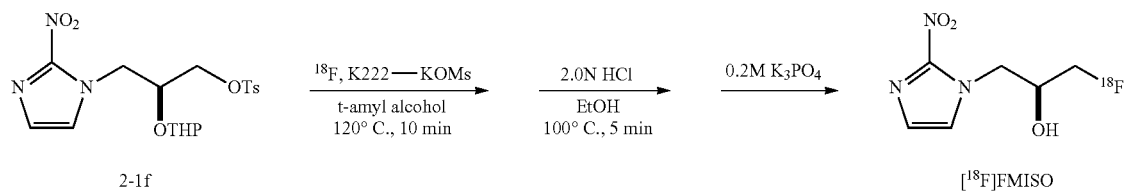

(wherein, OTs and THP are as defined above)

Example 5-6

Synthesis of [$^{18}$F]FC119

[$^{18}$F]FC119 was synthesized in the same manner as in Example 5-2, with the exception that precursor 2-1g (5 mg) was used (Reaction Scheme 5-6).

A radiation dose of 0.01 mCi was detected in the empty cartridge while the released solution exhibited a radiation dose of 3.79 mCi. The radio-TLC (%) was measured at 71% (radiochemical yield (%)=70.9%).

[Reaction Scheme 5-6]

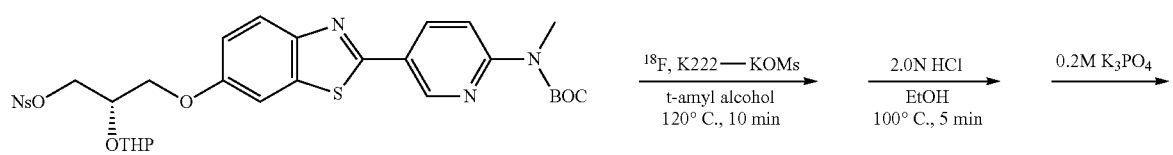

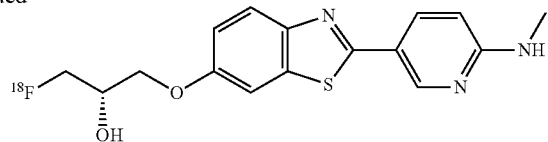

[$^{18}$F]FC119

(wherein, NsO, THP and BOC are as defined above)

Example 5-7

Synthesis of [$^{18}$F]AV-1

[$^{18}$F] AV-1 was synthesized in the same manner as in Example 5-2, with the exception that precursor 2-1h (5 mg) was used (Reaction Scheme 5-7).

A radiation dose of 0.01 mCi was detected in the empty cartridge while the released solution exhibited a radiation dose of 2.83 mCi. The radio-TLC (%) was measured at 62% (radiochemical yield (%)=62.0%).

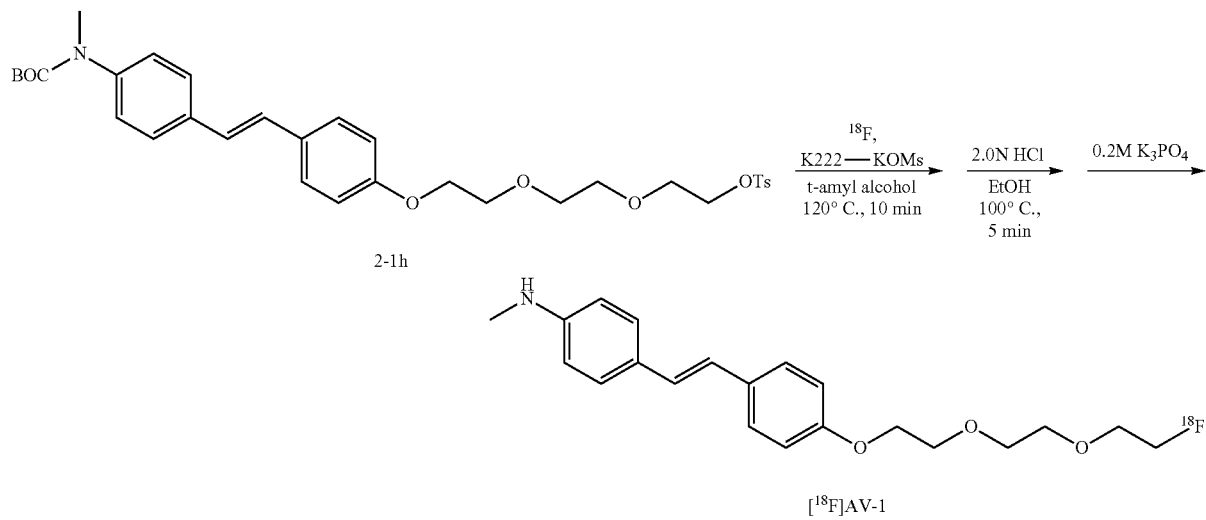

[Reaction Scheme 5-7]

(wherein, OTs and BOC are as defined above)

Example 5-8

Synthesis of [$^{18}$F]AV-45

[$^{18}$F] AV-45 was synthesized in the same manner as in Example 5-2, with the exception that precursor 2-1i (5 mg) was used (Reaction Scheme 5-8).

A radiation dose of 0.02 mCi was detected in the empty cartridge while the released solution exhibited a radiation dose of 3.07 mCi. The radio-TLC (%) was measured at 64% (radiochemical yield (%)=63.6%).

[Reaction Scheme 5-8]

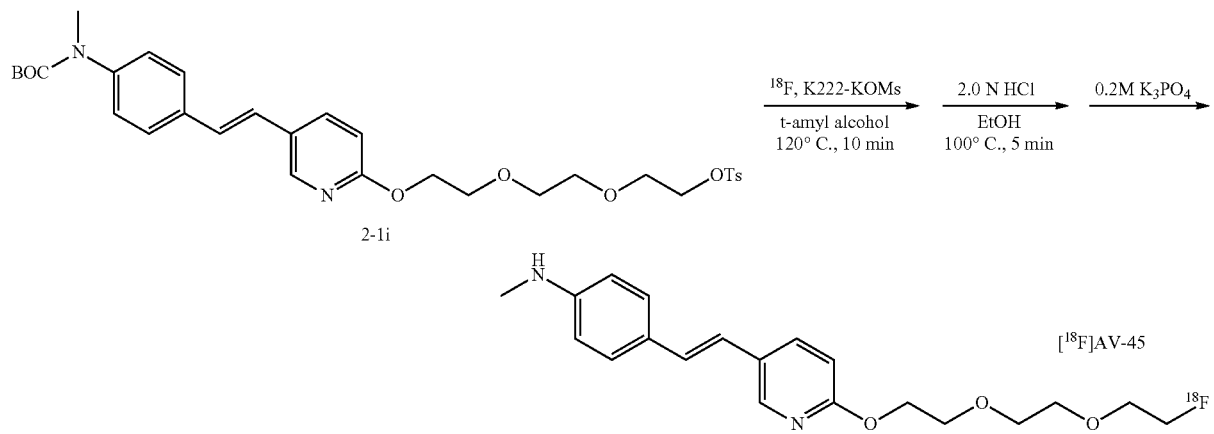

(wherein, OTs and BOC are as defined above)

Example 5-9

Synthesis of [$^{18}$F]Fallypride

[$^{18}$F]Fallypride was synthesized in the same manner as in Example 5-3, with the exception that precursor 2-1j (5 mg) was used (Reaction Scheme 5-9).

A radiation dose of 0.92 mCi was detected in the empty cartridge while the released solution exhibited a radiation dose of 2.88 mCi. The radio-TLC (%) was measured at 97% (radiochemical yield (%)=73.5%).

Example 5-10

Synthesis of [$^{18}$F]Flumazenil

[$^{18}$F]Flumazenil was synthesized in the same manner as in Example 5-3, with the exception that precursor 2-1k (5 mg) was used (Reaction Scheme 5-10).

A radiation dose of 1.21 mCi was detected in the empty cartridge while the released solution exhibited a radiation dose of 3.04 mCi. The radio-TLC (%) was measured at 94% (radiochemical yield (%)=67.2%).

[Reaction Scheme 5-9]

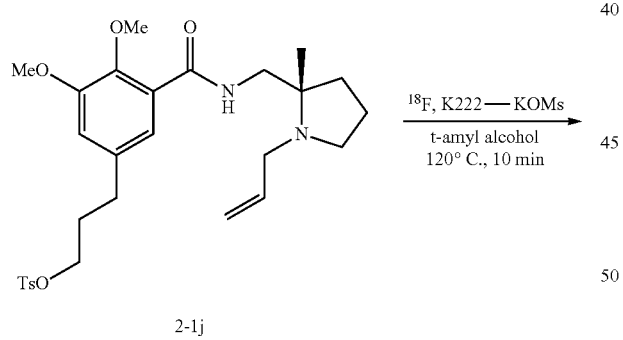

(wherein, OTs is as defined above)

[Reaction Scheme 5-10]

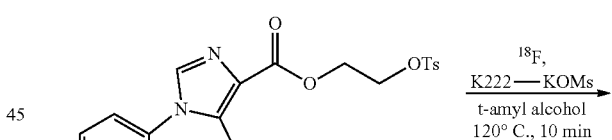

(wherein, OTs is as defined above)

Example 5-11

Synthesis of Ethyl-[$^{18}$F]fluorobenzoate

Ethyl-[$^{18}$F]fluorobenzoate was synthesized in the same manner as in Example 5-3, with the exception that precursor 2-(5 mg) was used at a reaction temperature of 100° C. in cacetonitrile as a reaction solvent (Reaction Scheme 5-11).

A radiation dose of 0.94 mCi was detected in the empty cartridge while the released solution exhibited a radiation dose of 2.80 mCi. The radio-TLC (%) was measured at 97% (radiochemical yield (%)=72.6%).

[Reaction Scheme 5-11]

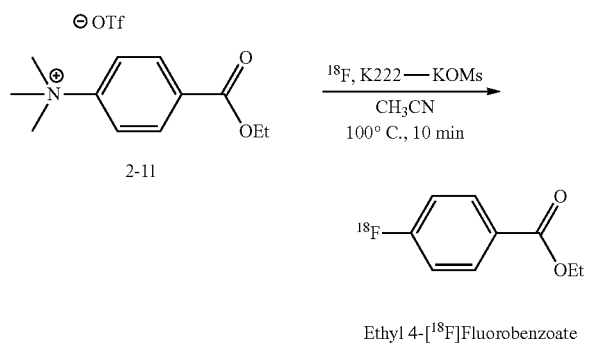

Ethyl 4-[$^{18}$F]Fluorobenzoate (wherein, OTf is as defined above)

Example 5-12

Synthesis of [$^{18}$F]FBA

[$^{18}$F]FBA was synthesized in the same manner as in Example 5-3, with the exception that precursor 2-1m (5 mg) was used at a reaction temperature of 100° C. in acetonitrile as a reaction solvent (Reaction Scheme 5-12).

A radiation dose of 0.91 mCi was detected in the empty cartridge while the released solution exhibited a radiation dose of 3.21 mCi. The radio-TLC (%) was measured at 96% (radiochemical yield (%)=74.8%).

[Reaction Scheme 5-12]

(wherein, OTf is as defined above)

Example 5-13

Synthesis of [$^{18}$F]FET

[$^{18}$F]FET was synthesized in the same manner as in Example 5-2, with the exception that precursor 2-1n (5 mg) was used (Reaction Scheme 5-13).

A radiation dose of 0.02 mCi was detected in the empty cartridge while the released solution exhibited a radiation dose of 2.85 mCi. The radio-TLC (%) was measured at 69% (radiochemical yield (%)=68.5%).

[Reaction Scheme 5-13]

(wherein, OTs and Tr are as defined above)

Example 5-14

Synthesis of [$^{18}$F]FMT

[$^{18}$F]FMT was synthesized in the same manner as in Example 5-2, with the exception that precursor 2-10 (5 mg) was used (Reaction Scheme 5-14).

A radiation dose of 0.03 mCi was detected in the empty cartridge while the released solution exhibited a radiation dose of 2.58 mCi. The radio-TLC (%) was measured at 52% (radiochemical yield (%)=51.4%).

[Reaction Scheme 5-14]

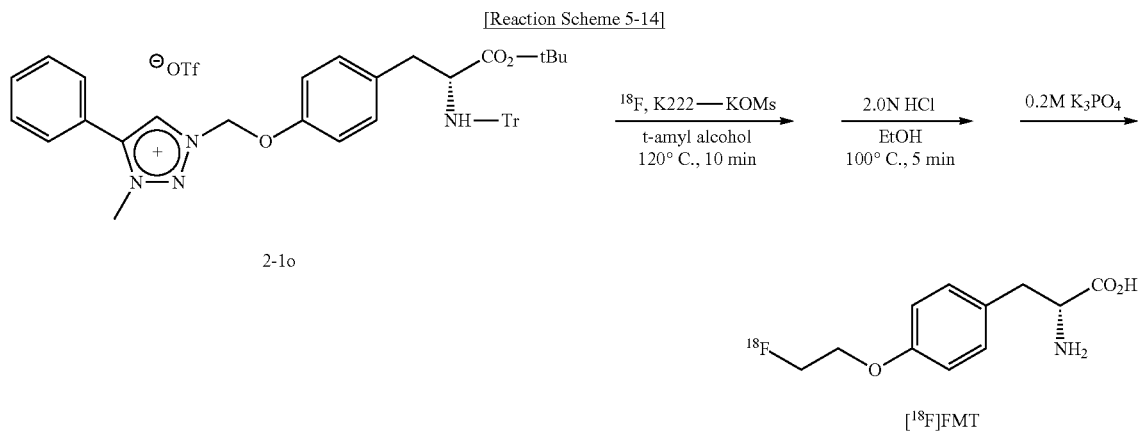

(wherein, OTs and Tr are as defined above)

Example 5-15

Synthesis of [$^{18}$F]Fluoroethylpropargyldiethyleneglycol

[$^{18}$F]Fluoroethylpropargyldiethyleneglycol was synthesized in the same manner as in Example 5-2, with the exception that precursor 2-1p (4 mg) was used (Reaction Scheme 5-15). A radiation dose of 1.35 mCi was detected in the empty cartridge while the released solution exhibited a radiation dose of 2.69 mCi. The radio-TLC (%) was measured at 93% (radiochemical yield (%)=61.9%).

[Reaction Scheme 5-15]

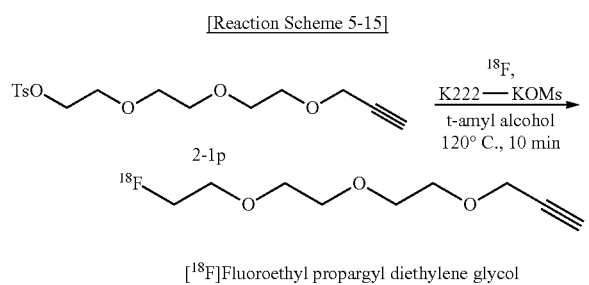

(wherein, OTs is as defined above)

Example 5-16

Synthesis of [$^{18}$F]Fluoroethylazidoethylethyleneglycol

Fluoroethylazidoethylethyleneglycol was synthesized in the same manner as in Example 5-3, with the exception that precursor 2-1q (4 mg) was used (Reaction Scheme 5-16). A radiation dose of 1.29 mCi was detected in the empty cartridge while the released solution exhibited a radiation dose of 2.83 mCi. The radio-TLC (%) was measured at 98% (radiochemical yield (%)=67.3%).

[Reaction Scheme 5-16]

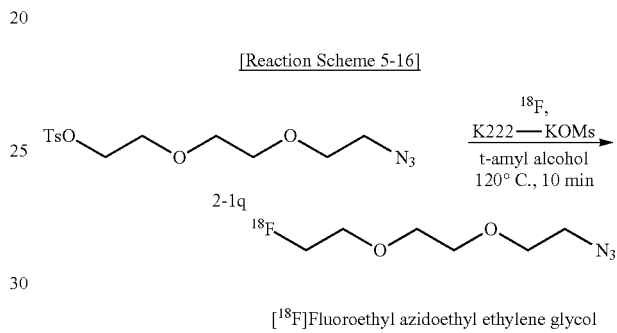

(wherein, OTs is as defined above)

Example 5-17

Synthesis of [$^{18}$F]ADIBO

[$^{18}$F]ADIBO was synthesized in the same manner as in Example 5-3, with the exception that precursor 2-1r (4 mg) was used (Reaction Scheme 5-17). A radiation dose of 1.46 mCi was detected in the empty cartridge while the released solution exhibited a radiation dose of 2.61 mCi. The radio-TLC (%) was measured at 93% (radiochemical yield (%)=59.3%).

[Reaction Scheme 5-17]

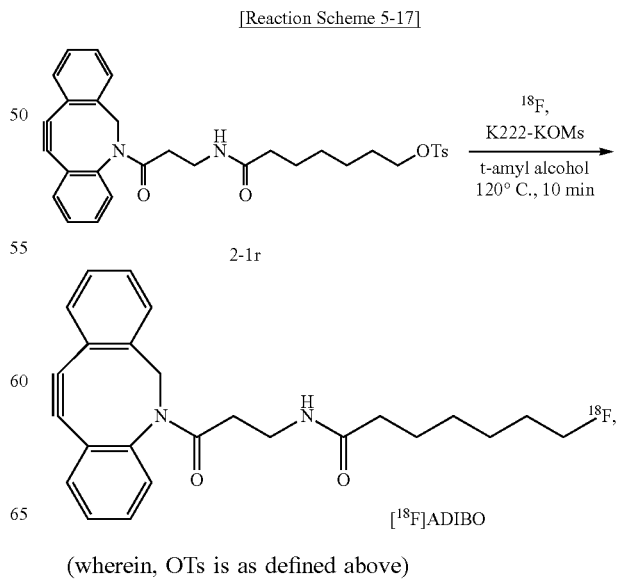

(wherein, OTs is as defined above)

Example 5-18

Synthesis of [$^{18}$F]RGD-ADIBO

[$^{18}$F]ADIBO was prepared from the precursor 2-1r (1 mg) in a manner similar to that of Example 5-17. The cartridge was transferred to a furnace maintained at room temperature, with the reaction solution still confined therein. Then, reaction solution 2 [H$_2$O/MeOH (1/1, 0.5 mL) in which N$_3$-cRGDfK (3 mg) was dissolved] was introduced upwardly from the bottom of the cartridge after which nitrogen gas was also fed from the bottom slowly for 15 min. After being withdrawn from the furnace, the cartridge was allowed to drain the solution therefrom and washed with acetonitrile (3 mL) (Reaction Scheme 5-18).

A radiation dose of 1.46 mCi was detected in the empty cartridge while the released solution exhibited a radiation dose of 2.17 mCi. The radio-TLC (%) was measured at 74% (radiochemical yield (%)=44.2%).

[Reaction Scheme 5-18]

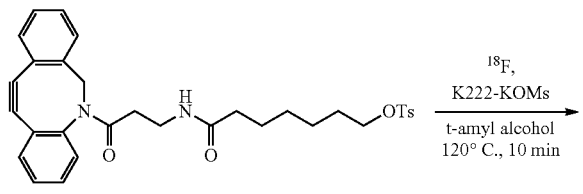

2-1r

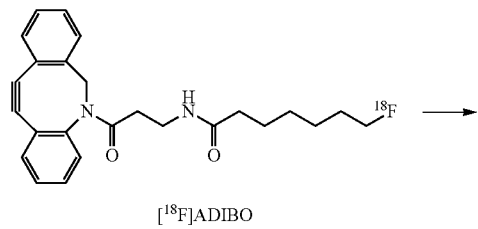

[$^{18}$F]ADIBO

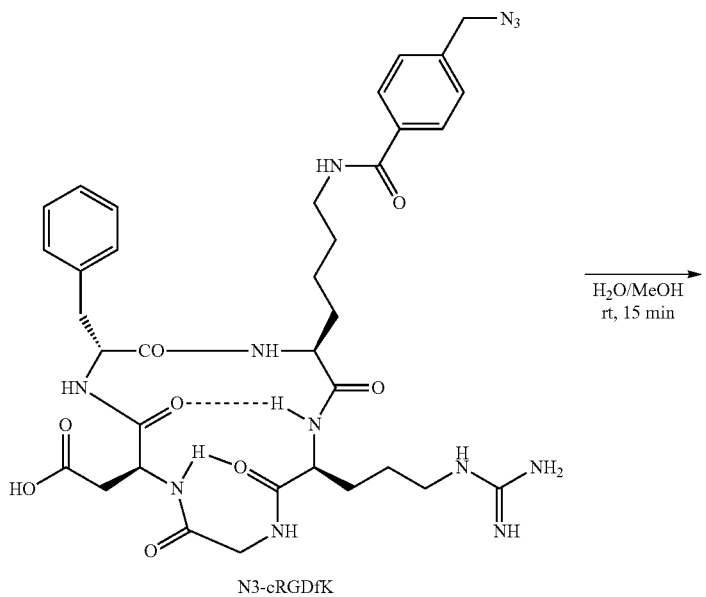

N3-cRGDfK

-continued

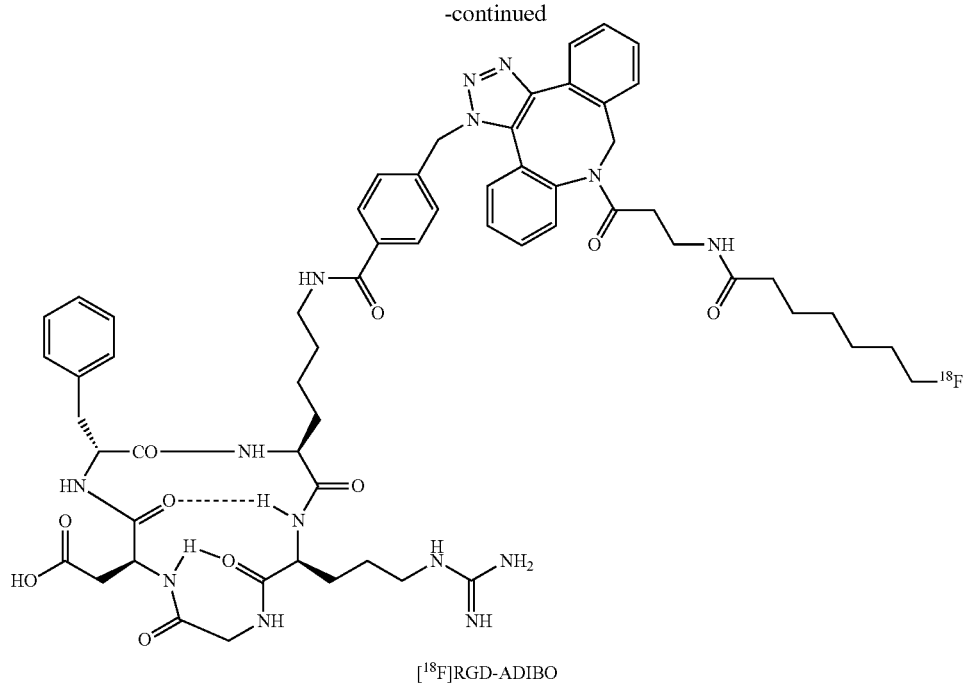

[$^{18}$F]RGD-ADIBO (wherein, OTs is as defined above)

Example 5-19

Synthesis of [$^{123}$I] FP-CIT

The polymer-precursor mixture 3e (50 mg), prepared in Example 3-6, was loaded into a cartridge. Using a syringe, 3 mL of distilled water was allowed to flow through the polymer. Then, an aqueous solution of [$^{123}$I]NaI (0.72 mCi, 0.5 mL) was added to the mixture. After the cartridge was purged with nitrogen for 1 min, reaction solution 1 (ethanol 0.5 mL in which chloramin-T (2 mg), and 1-butyl-3-methylimidazolium methanesulfonate (2 mg) were dissolved) was introduced upwardly from the bottom of the cartridge which was then fastened with a valve. Using a syringe, nitrogen gas was also fed from the bottom slowly for 10 min. The cartridge was allowed to drain the solution therefrom and washed with acetonitrile (3 mL). The reaction procedure is illustrated in Reaction Scheme 5-19.

A radiation dose of 0.02 mCi was detected in the empty cartridge while the released solution exhibited a radiation dose of 0.68 mCi. The radio-TLC (%) was measured at 99% (radiochemical yield (%)=96.2%).

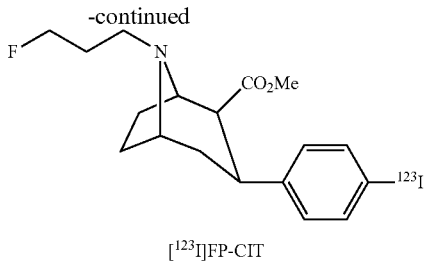

[$^{123}$I]FP-CIT

Example 5-20

Synthesis of [$^{123}$I]Iodomazenil

[$^{123}$I]Iodomazenil was synthesized in the same manner as in Example 5-19, with the exception that polymer-precursor mixture 3f (50 mg), prepared in Example 3-7, was used (Reaction Scheme 5-20). A radiation dose of 0.01 mCi was detected in the empty cartridge while the released solution exhibited a radiation dose of 0.47 mCi. The radio-TLC (%) was measured at 99% (radiochemical yield (%)=96.9%).

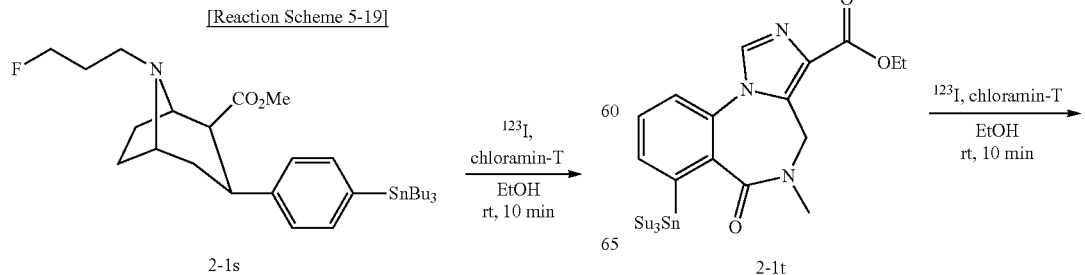

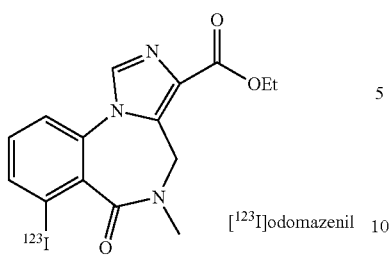

[123I]odomazenil

Example 5-21

Synthesis of [68Ga]NOTA-cRGDyK

Polymer 1-2a (100 mg), prepared in Example 1-6, was loaded to a cartridge. Using a syringe, 3 mL of distilled water was allowed to flow through the polymer. Then, an aqueous 68Ga HCl solution (4.39 mCi) eluted with 0.1 N HCl (1 mL) from a 68Ga generator was slowly flowed into the cartridge, followed by adding distilled water (2 mL). Reaction solution 1 [sodium acetate/acetic acid buffer in which NOTA-cRGDyK (0.5 mg) was dissolved, pH=4.5-5.5, 0.5 mL] was introduced upwardly from the bottom of the cartridge which was then fastened with a valve. The cartridge was placed in a furnace maintained at 50° C., and using a syringe, nitrogen gas was introduced upwardly from the bottom of the cartridge which was then allowed to drain the solution therefrom and washed with ethanol (2 mL) (Reaction Scheme 5-21). A radiation dose of 0.21 mCi was detected in the empty cartridge while the released solution exhibited a radiation dose of 2.89 mCi. The radio-TLC (%) was measured at 99% (radiochemical yield (%)=92.3%).

[Reaction Scheme 5-21]

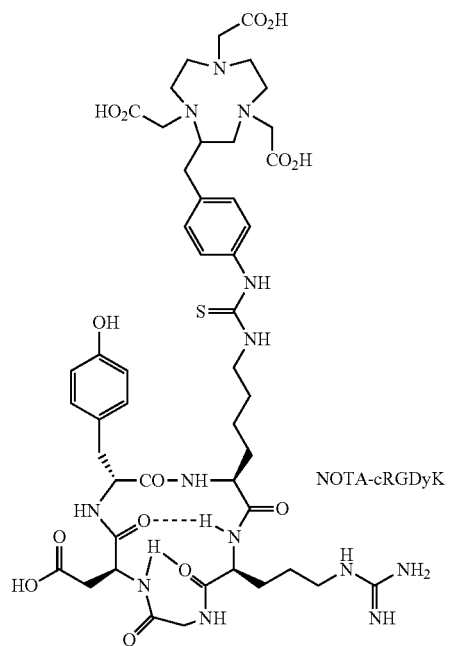

Example 5-22

Synthesis of [64Cu]NOTA-cRGDyK

[64Cu]NOTA-cRGDyK was synthesized in the same manner as in Example 5-21, with the exception that an aqueous HCl solution of 64Cu (2.24 mCi) prepared in cyclotron was used (Reaction Scheme 5-22). A radiation dose of 0.09 mCi was detected in the empty cartridge while the released solution exhibited a radiation dose of 2.13 mCi. The radio-TLC (%) was measured at 99% (radiochemical yield (%)=95.0%).

[Reaction Scheme 5-22]

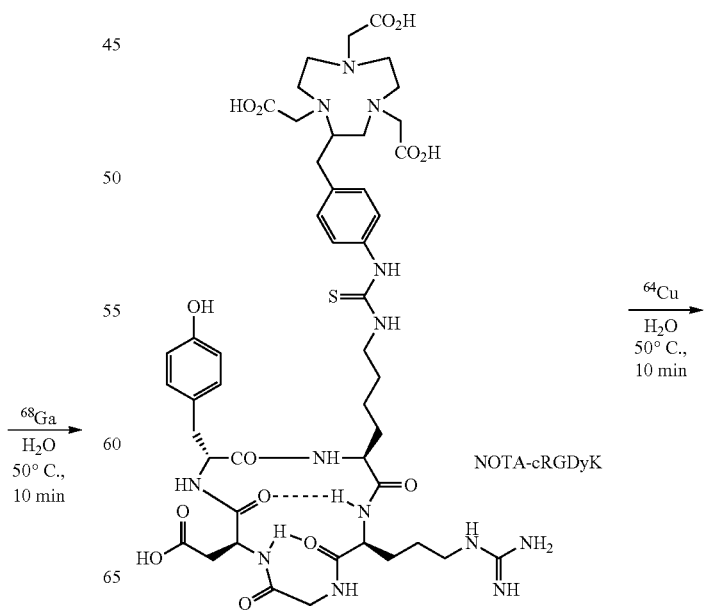

45 / 46
-continued

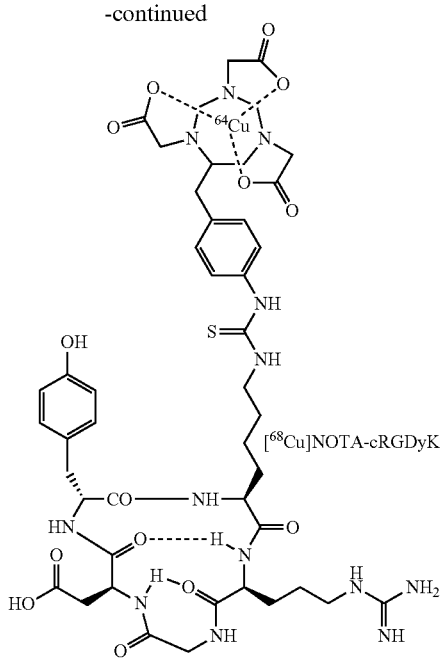

Example 5-23

Synthesis of [$^{177}$Lu]DOTA-cRGDyK

Polymer 1-2a (100 mg), prepared in Example 1-6, was loaded to a cartridge. Using a syringe, 3 mL of distilled water was allowed to flow through the polymer. Then, an aqueous $^{177}$Lu HCl solution (0.88 mCi) prepared in a cyclotron was slowly flowed into the cartridge, followed by adding distilled water (2 mL). Reaction solution 1 [sodium acetate/acetic acid buffer in which DOTA-cRGDyK (0.5 mg) was dissolved, pH=4.5-5.5, 0.5 mL] was introduced upwardly from the bottom of the cartridge which was then fastened with a valve. The cartridge was placed in a furnace maintained at 80° C., and using a syringe, nitrogen gas was introduced upwardly from the bottom of the cartridge which was then allowed to drain the solution therefrom and washed with ethanol (2 mL) (Reaction Scheme 5-23). A radiation dose of 0.04 mCi was detected in the empty cartridge while the released solution exhibited a radiation dose of 0.83 mCi. The radio-TLC (%) was measured at 99% (radiochemical yield (%)=96.7%).

[Reaction Scheme 5-23]

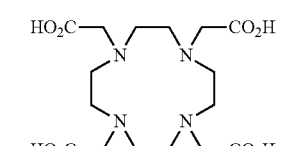

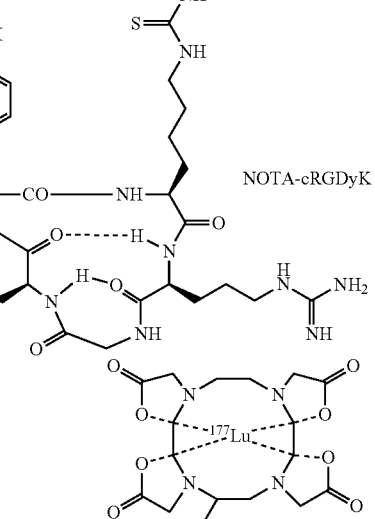

NOTA-cRGDyK

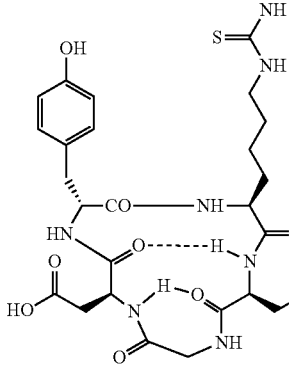

[$^{177}$Lu]DOTA-cRGDyK

The invention claimed is:
1. A method for synthesizing a radiopharmaceutical using a polymer-filled cartridge, comprising:
    passing a radioisotope solution through the polymer-filled cartridge to trap a radioisotope;
    loading a reaction solution to the cartridge which comprises a solution of a precursor and/or phase transfer catalyst dissolved in solvent;
    labeling a precursor with the radioisotope entrapped by the cartridge; and
    eluting a radioisotope-labeled compound from the cartridge to provide the radiopharmaceutical, wherein the cartridge is filled with a polymer and has a structure in which an upper porous frit and a lower porous frit are placed, said polymer being located between the upper and the lower porous frit, the structure having a space over the location of the polymer and wherein the upper porous frit and the lower porous frit are not permeated with the polymer filled within the cartridge, but are permeated with a solution, wherein the polymer has a structure represented by the following Chemical Formula 1-1 or 1-2:

[Chemical Formula 1-1]

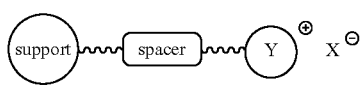

1-1

[Chemical Formula 1-2]

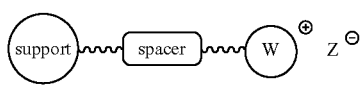

1-2 wherein,
'support' is a non-soluble organic polymer selected from the group consisting of polystyrene, polyethylene glycol, and a combination thereof, or a non-soluble silica;
'spacer' is a halogen-substituted or unsubstituted hydrocarbon of $C_{1-30}$ in which at least one element selected from the group consisting of nitrogen, oxygen and sulfur may be intermediated;
'Y' is a halogen-substituted or unsubstituted organic salt selected from among —$NR_1R_2R_3$ or an imidazolium salt

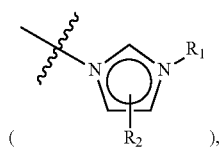

a triazolium salt

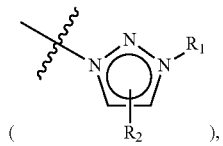

and a pyridinium salt

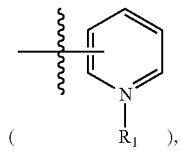

wherein $R_1$, $R_2$, and $R_3$, are independently a hydrocarbon of $C_{1-30}$ in which at least one element selected from the group consisting of nitrogen, oxygen and sulfur may be intermediated;

'X' is tetrafluoroborate ($BF_4$), hexafluorophosphate ($PF_6$), hexafluoroantimony ($SbF_6$), bis(trifluoromethane)sulfone imide ($N(Tf)_2$), potassium carbonate ($KCO_3$), bicarbonate ($HCO_3$), potassium phosphate ($KHPO_4$ or $K2PO_4$), or alkane sulfonate ($R_1SO_3$), wherein $R_1$ is a hydrocarbon of $C_{1-30}$ in which at least one element selected from the group consisting of nitrogen, oxygen, sulfur, phosphorous and a combination thereof may be intermediated;

'W' is phosphate (—$PO_3$), carboxylate (—$CO_2$), or sulfonate (—$SO_3$); and

'Z' is hydrogen, lithium (Li), sodium (Na), potassium (K), rubidium (Rb), cesium (Cs), or quaternary ammonium salt of —$NR_1R_2R_3$, wherein $R_1$, $R_2$ and $R_3$ are halogen-substituted or unsubstituted, and independently a hydrocarbon of $C_{1-30}$ in which at least one element selected from the group consisting of nitrogen, oxygen and sulfur may be intermediated.

2. The method of claim 1, wherein the precursor compound has a structure represented by the following Chemical Formula 2-1 or 2-2:

[Chemical Formula 2-1]

2-1

[Chemical Formula 2-2]

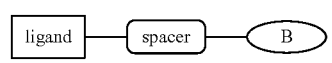

2-2

[wherein,
'X' is a sulfonate ($R_1$—$S(O)_2O$—), aryl iodonium ($R_1$—$I^+$—), quaternary ammonium salt ($R_1R_2R_3N^+$—), hydrogen, nitro (—$NO_2$), alkoxy ($R_1O$—), triazolium salt

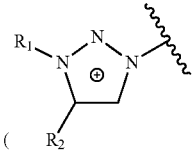

or organic tin ($R_1R2R_3Sn$—), wherein $R_1$, $R_2$ and $R_3$ are halogen-substituted or unsubstituted and independently a hydrocarbon of $C_{1-30}$ in which at least one element selected from the group consisting of nitrogen, oxygen, sulfur, phosphorus and a combination thereof may be intermediated;

'A' is a moiety other than the radioisotope in the radiopharmaceutical compound with or without a protecting group;

'ligand' is a part made of a hydrocarbon containing at least one element selected among nitrogen, oxygen and sulfur and capable of chelation with a radioactive metal ion;

'spacer' is an oligopeptide, oligoethylene glycol, or a halogen-substituted or unsubstituted hydrocarbon of $C_{1-30}$ in which at least one selected from the group consisting of nitrogen, oxygen, sulfur, phosphorus, and a combination thereof may be intermediated; and 'B' is a biological compound selected from among an amino acid, a sugar, a lipid, and a nucleic acid.

3. The method of claim 2, wherein the precursor compound is selected from the group consisting of
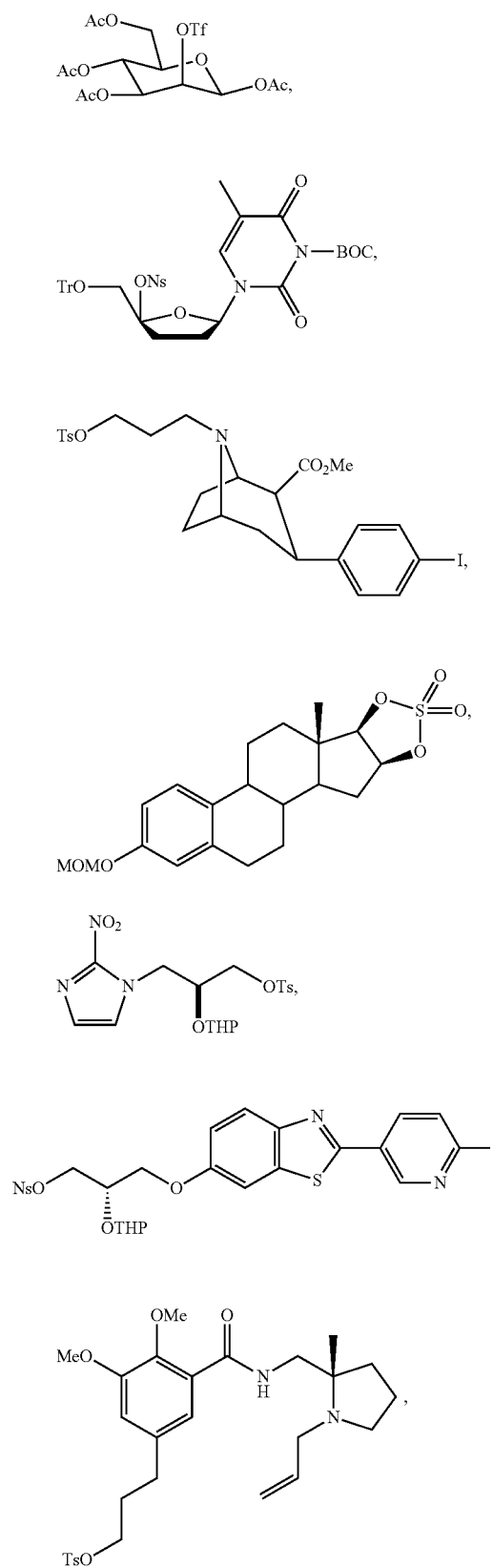
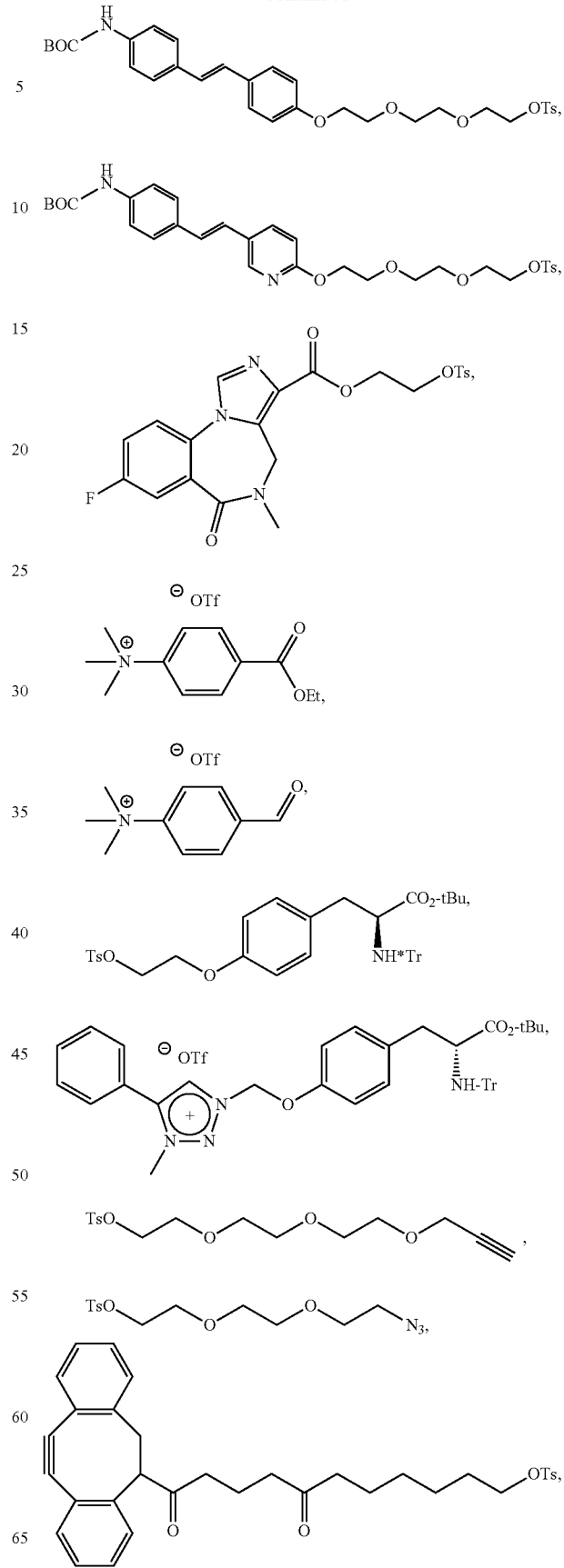

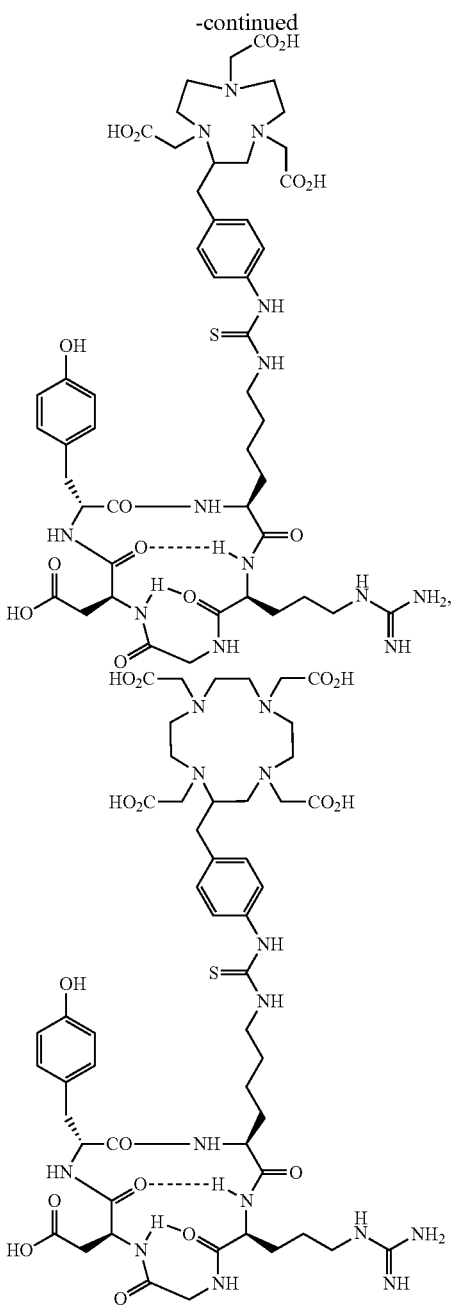

[wherein, —OTf stands for —OS(O)$_2$—CF$_3$, —ONs for —OS(O)$_2$—C$_6$H$_4$-p-NO$_2$, -Tr for —C(Ph)$_3$, —BOC for —C(O)O-tBu, MOM for —CH$_2$OCH$_3$, -THP for -tetrahydropyranyl, and —OTs for —OS(O)$_2$—C$_6$H$_4$-p-CH$_3$].

4. The method of claim 2, wherein the ligand of Chemical Formula 2-2 is selected from the group consisting of diethylenetriamine pentaacetic acid (DTPA), ethylenediamine tetraacetic acid (EDTA), 1,4,7-triazacyclononane-N,N',N''-triacetic acid (NOTA), 1,4,7,10-tetraazacyclododecane-N,N',N'', N'''-tetraacetic acid (DOTA), 1,4,8,11-tetraazacyclotetradodecane-N,N',N'',N'''-tetraacetic acid (TETA), and bis(thiosemicarbazone) (ATSM), and mercaptoacetyltriglycine (MAG3).

5. The method of claim 1, wherein the reaction solution 1 has a solvent selected from the group consisting of acetonitrile, tetrahydrofuran, 1,4-dioxane, diethylether, 1,2-methoxyethane, chloroform, 1,2-dichloroethane, 1,1-dichloroethane, dichloromethane, benzene, toluene, xylene, mesitylene, chlorobenzene, dichlorobenzene, acetone, methylethylketone, nitromethane, dimethylformamide, dimethylacetamide, dimethylsulfoxide, sulfolane, 1,3-dimethyl-2-imidazolidinone, triethylamine, diisopropylethylamine, pyridine, picoline, collidine, methanol, ethanol, n-propanol, n-butanol, amylalcohol, n-hexylalcohol, n-heptanol, n-octanol, isopropanol, isobutanol, isoamylalcohol, 3-pentanol, t-butanol, t-amylalcohol, 2,3-dimethyl-2-butanol, 2-(trifluoromethyl)-2-propanol, 3-methyl-3-pentanol, 3-ethyl-3-pentanol, 2-methyl-2-pentanol, 2,3-dimethyl-3-pentanol, 2,4-dimethyl-2-pentanol, 2-methyl-2-hexanol, 2-cyclopropyl-2-propanol, 2-cyclopropyl-2-butanol, 2-cyclopropyl-3-methyl-2-butanol, 1-methylcyclopentanol, 1-ethylcyclopentanol, 3-propyicyclopentanol, 1-methylcyclohexanol, 1-ethylcyclohexanol, 1-methylcycloheptanol, oligoethylene glycol of R$_1$—(OCH$_2$CH$_2$)$_n$—OR$_2$ [wherein R$_1$ and R$_2$ are independently a halogen-substituted or unsubstituted hydrocarbon of C$_{1-30}$ in which at least one element selected from the group consisting of nitrogen, oxygen, sulfur, phosphorus, and a combination thereof may be intermediated, and n is 1-3000], an ionic liquid of

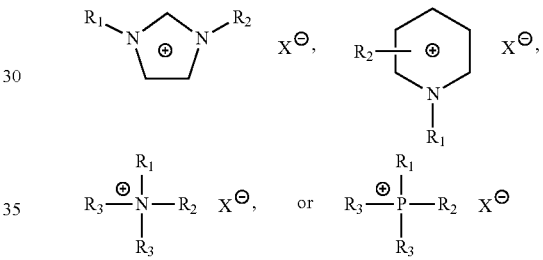

[wherein R$_1$,R$_2$,R$_3$, and R$_4$ are independently a halogen-substituted or unsubstituted hydrocarbon of C$_{1-30}$ in which at least one element selected from the group consisting of nitrogen, oxygen, sulfur, phosphorus, and a combination thereof may be intermediated, and X is selected from methanesulfonate, trifluoromethane sulfonate, hexafluorophosphate, hexafluoroantimonate, tetrafluoroborate, paratoluenesulfonate, bis(trifluorosulfonyl)imide], water, and a combination thereof.

6. The method of claim 1, wherein the phase transfer catalyst is a kryptopix compound selected from the group consisting of kryptopix[2.2.2] (4,7,13,16,21,24-hexaoxa-1,10-diazabicyclo[8.8.8]hexacosane), 4,7,13,16,21-pentaoxa-1,10-diazabicyclo[8.8.5]tricosane, 4,7,13,18-tetraoxa-1,10-diazabicyclo[8.5.5]eicosane, and 5,6-benzo-4,7,13,16,21,24-hexaoxa-1,10-diazabicyclo[8.8.8]hexacos-5-ene; a crown ether compound selected from the group consisting of 4'-aminobenzo-15-crown-5, 4'-aminobenzo-15-crown-5, 4'-aminobenzo-15-crown-5 hydrochloride, 4'aminobenzo-18-crown-6, 4'-aminodibenzo-18-crown-6,2-aminomethyl-15-crown-5, 2-aminomethyl-15-crown-5, 2-aminomethyl-18-crown-6, 4'-amino-5'-nitrobenzo-15-crown-5, 4'-amino-5'-nitrobenzo-15-crown-5, 1-aza-12-crown-4, 1-aza-15-crown-5, 1-aza-15-crown-5, 1-aza-18-crown-6, 1-aza-18-crown-6, benzo-12-crown-4, 5,6-benzo-4,7,13,16,21,24-hexaoxa-1,10-diazabicylclo[8.8.8]hexacos-5-ene, 1-benzyl-1-aza-12-crown-4, bis[(benzo-15-crown-5)-15-ylmethyl] pimelate, 4'-bromobenzo-15-crown-5, 4-tert-butylbenzo-15-crown-5, 4-tert-butylcyclohexano-15-crown-5, 4'carboxybenzo-15-crown-5' polyethylene glycols, and a crown ether compound of polyethylene oxides; $R_1$—$(OCH_2CH_2)_n$—$OR_2$ oligoethylene glycol [wherein $R_1$ and R2 are independently a halogen-substituted or unsubstituted hydrocarbon of $C_{1-30}$ in which at least one element selected from the group consisting of nitrogen, oxygen, sulfur, phosphorus, and a combination thereof may be intermediated, and n is 1-3000];

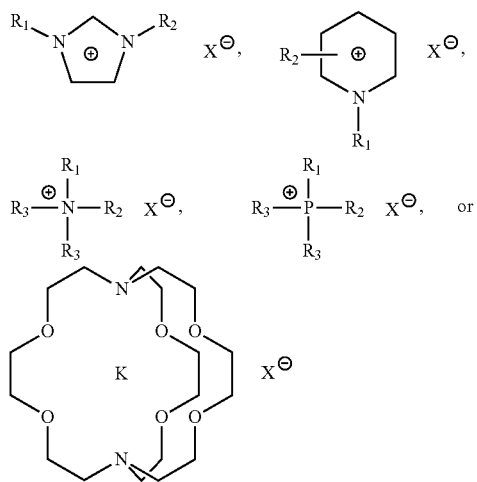

[wherein $R_1$, $R_2$, $R_3$, and $R_4$ are independently a halogen-substituted or unsubstituted hydrocarbon of $C_{1-30}$ in which at least one element selected from the group consisting of nitrogen, oxygen, sulfur, phosphorus and a combination thereof may be intermediated, X is methanesulfonate, trifluoromethanesulfonate, hexafluorophosphate, hexafluoroantimonate, tetrafluoroborate, paratoluenesulfonate, bis(trifluorosulfonyl)imide, potassium carbonate ($KCO_3$), bicarbonate ($HCO_3$), or potassium phosphate ($KHPO_4$ or $K_2PO_4$).

7. The method of claim 1, wherein the radioisotope is selected from the group consisting of F-18, Sc-44, Ti-45, Fe-52, Co-55, Cu-61, Cu-62, Cu-64, Ga-66, Ga-67, Cu-67, Ga-68, Br-77, Sr-83, Y-86, Zr-89, Y-90, Tc-99m, In-110, In-111, I-123, I-124, I-125, I-131, Lu-177, and Re-188.

8. The method of claim 1, further comprising, loading a second reaction solution for deprotection to the cartridge; and
deprotecting the radioisotope-labeled compound in the cartridge; or
loading a third reaction solution for conjugation to the cartridge, and conjugating
the radioisotope-labeled compound with a disease-targeting compound in the cartridge.

9. The method of claim 8, wherein the second reaction solution contains an acid or a base, the acid being selected from the group consisting of hydrochloric acid, bromic acid, iodic acid, sulfuric acid, phosphoric acid, acetic acid, benzoic acid, dichloroacetic acid, trichloroacetic acid, trifluoroacetic acid, methanesulfonic acid, trifluoromethanesulfonic acid, benzenesulfonic acid, and p-toluenesulfonic acid, the base being selected from the group consisting of trimethylamine, triethylamine, diisopropylethylamine, 4-(N,N-dimethylamino)pyridine, 1,8-diazabicyclo[5.4.0]undec-7-ene (DBU), 1,5-diazabicyclo[4.3.0]non-5-ene (DBN), 1,4-diazabicyclo[2.2.2]octane (Dabco), N-methylmorpholine, pyridine, picoline, collidine, guanidine, 1,1,3,3-tetramethyl-guanidine, MOH, M'$(OH)_2$, $MHCO_3$, $M_2CO_3$, $M'CO_3$, $M_3PO_4$, $M_2HPO_4$, and MOR [wherein M is selected from the group consisting of Li, Na, K, Cs, $NH_4$, $NMe_4$, $NEt_4$, $NBu_4$, and $NMe_3Bn$, M' is selected from the group consisting of Mg, Ca, and Ba, and R is selected from the group consisting of methyl, ethyl, isopropyl, and t-butyl], and has a solvent selected from the group consisting of acetonitrile, tetrahydrofuran, 1,4-dioxane, diethylether, 1,2-methoxyethane, chloroform, 1,2-dichloroethane, 1,1-dichloroethane, dichloromethane, benzene, toluene, xylene, mesitylene, chlorobenzene, dichlorobenzene, acetone, methylethylketone, nitromethane, dimethylformamide, dimethylacetamide, dimethylsulfoxide, sulfolane, 1,3-dimethyl-2-imidazolidinone, triethylamine, diisopropylethylamine, pyridine, picoline, collidine, methanol, ethanol, n-propanol, n-butanol, amylalcohol, n-hexylalcohol, n-heptanol, n-octanol, isopropanol, isobutanol, isoamylalcohol, 3-pentanol, t-butanol, t-amylalcohol, 2,3-dimethyl-2-butanol, 2-(trifluoromethyl)-2-propanol, 3-methyl-3-pentanol, 3-ethyl-3-pentanol, 2-methyl-2-pentanol, 2,3-dimethyl-3-pentanol, 2,4-dimethyl-2-pentanol, 2-methyl-2-hexanol, 2-cyclopropyl-2-propanol, 2-cyclopropyl-2-butanol, 2-cyclopropyl-3-methyl-2-butanol, 1-methylcyclopentanol, 1-ethylcyclopentanol, 3-propylcyclopentanol, 1-methylcyclohexanol, 1-ethylcyclohexanol, 1-methylcycloheptanol, oligoethylene glycol of $R_1$—$(OCH_2CH_2)_n$—$OR_2$ [wherein $R_1$ and R2 are independently a halogen-substituted or unsubstituted hydrocarbon of $C_{1-30}$ in which at least one element selected from the group consisting of nitrogen, oxygen, sulfur, phosphorus and a combination thereof may be intermediated, and n is 1-3000], an ionic liquid of

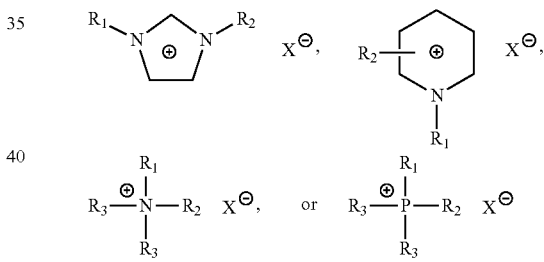

[wherein $R_1$, $R_2$, $R_3$, and $R_4$ are independently a halogen-substituted or unsubstituted hydrocarbon of $C_{1-30}$ in which at least one element selected from the group consisting of nitrogen, oxygen, sulfur, phosphorus and a combination thereof may be intermediated, and X is methanesulfonate, trifluoromethane sulfonate, hexafluorophosphate, hexafluoroantimonate, tetrafluoroborate, paratoluenesulfonate, or bis(trifluorosulfonyl)imide], water, and a combination thereof.

10. The method of claim 8, wherein the third reaction solution contains a disease-targeting compound that is capable of conjugation with the radioisotope-labeled compound, and has a solvent selected from the group consisting of acetonitrile, tetrahydrofuran, 1,4-dioxane, diethylether, 1,2-methoxyethane, chloroform, 1,2-dichloroethane, 1,1-dichloroethane, dichloromethane, benzene, toluene, xylene, mesitylene, chlorobenzene, dichlorobenzene, acetone, methylethylketone, nitromethane, dimethylformamide, dimethylacetamide, dimethylsulfoxide, sulfolane, 1,3-dimethyl-2-imidazolidinone, triethylamine, diisopropylethylamine, pyridine, picoline, collidine, methanol, ethanol, n-propanol, n-butanol, amylalcohol, n-hexylalcohol, n-heptanol, n-octanol, isopropanol, isobutanol, isoamylalcohol, 3-pentanol, t-butanol, t-amylalcohol, 2,3-dimethyl-2-butanol, 2-(trifluoromethyl)-2-propanol, 3-methyl-3-pentanol, 3-ethyl-3-pentanol, 2-methyl-2-pentanol, 2,3-dimethyl-3-pentanol, 2,4-dimethyl-2-pentanol, 2-methyl-2-hexanol, 2-cyclopropyl-2-propanol, 2-cyclopropyl-2-butanol, 2-cyclopropyl-3-methyl-2-butanol, 1-methylcyclopentanol, 1-ethylcyclopentanol, 3-propylcyclopentanol, 1-methylcyclohexanol, 1-ethylcyclohexanol, 1-methylcycloheptanol, oligoethylene glycol of $R_1$—$(OCH_2CH_2)_n$—$OR_2$ [wherein $R_1$ and $R_2$ are independently a halogen-substituted or unsubstituted hydrocarbon of $C_{1-30}$ in which at least one element selected from the group consisting of nitrogen, oxygen, sulfur, phosphorus and a combination thereof may be intermediated, and n is 1-3000], an ionic liquid of

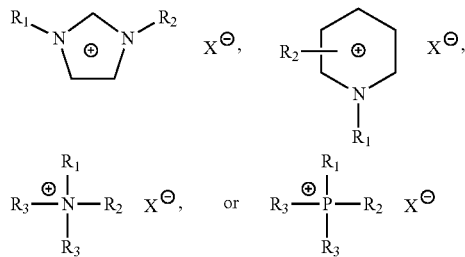

[wherein $R_1, R_2, R_3$, and $R_4$ are independently a halogen-substituted or unsubstituted hydrocarbon of $C_{1-30}$ in which at least one element selected from the group consisting of nitrogen, oxygen, sulfur, phosphorus and a combination thereof may be intermediated, and X is methanesulfonate, trifluoromethane sulfonate, hexafluorophosphate, hexafluoroantimonate, tetrafluoroborate, paratoluenesulfonate, or bis(trifluorosulfonyl)imide], water, and a combination thereof.

11. The method of claim 10, wherein the radioisotope-labeled compound has a structure represented by the following Chemical Formula 3:

[Chemical Formula 3]

3

[wherein, 'A' is a moiety other than the radioisotope in the radiopharmaceutical compound with or without a protecting group; and 'E' is F-18, I-123, I-124, I-125, or I-131].

12. The method of claim 11, wherein the radioisotope-labeled compound is selected from the group consisting of

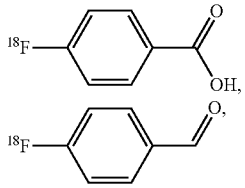

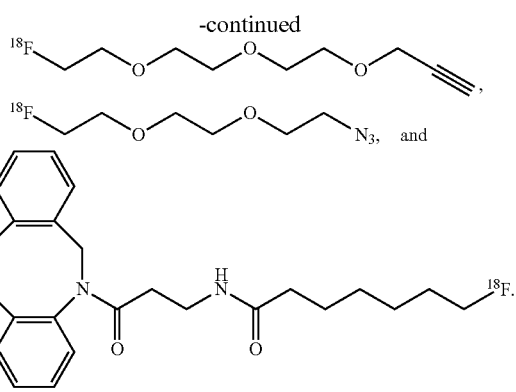

13. The method of claim 10, wherein the disease-targeting compound is a compound represented by the following Chemical Formula 4:

[Chemical Formula 4]

4

[wherein 'T' is a biological compound selected from the group consisting of an amino acid, a sugar, a lipid and a nucleic acid, and "J" is selected from $NHR_1$, OH, $CO_2$—$R_1$, $N_3$, C≡C—H, $PR_1R_2$, $NHNH_2$, $ONH_2$, and

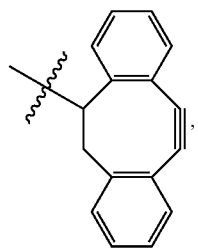

wherein $R_1$ and $R_2$ are independently a halogen-substituted or unsubstituted hydrocarbon of $C_{1-30}$ that may contain at least one element selected from the group consisting of nitrogen, oxygen, sulfur, phosphorus, and a combination thereof].

14. The method of claim 1, further comprising neutralizing the solution in the cartridge with an acid or a base, prior to eluting a radioisotope-labeled compound from the cartridge.

15. The method of claim 8, where the labeling the precursor, deprotecting the radioisotope-labeled compound and conjugating the radioisotope-labeled compound is carried out in such a manner that a gas is provided to mix the respective reaction solution well.

* * * * *

UNITED STATES PATENT AND TRADEMARK OFFICE
CERTIFICATE OF CORRECTION

| | |
|---|---|
| PATENT NO. | : 9,550,704 B2 |
| APPLICATION NO. | : 14/401790 |
| DATED | : January 24, 2017 |
| INVENTOR(S) | : Dae Yoon Chi et al. |

It is certified that error appears in the above-identified patent and that said Letters Patent is hereby corrected as shown below:

In the Specification

Chemical formula 1-2 should be amended so that there is a positive charge on the Z and a negative charge on the W as shown:

" 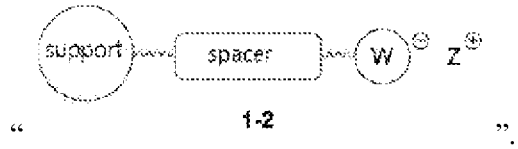 ".

Chemical formula 3 should be amended so that there is a nitrogen in the place of a carbon as shown:

" 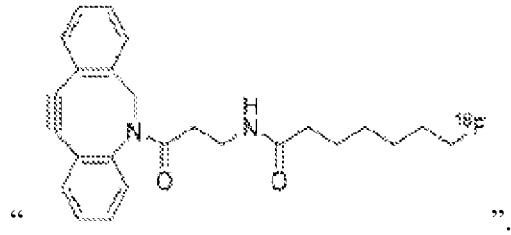 ".

Reaction Scheme 5-14 should be amended so that there is one less carbon on the radiation tag side chain of the product as shown:

" 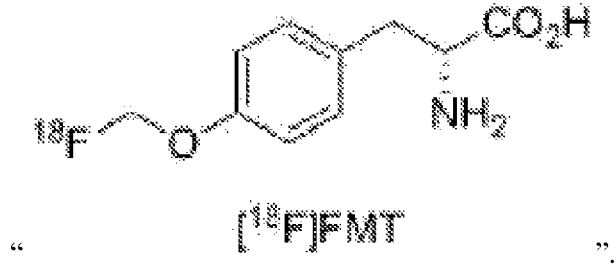 ".

Signed and Sealed this
Twenty-fifth Day of July, 2017

Joseph Matal
*Performing the Functions and Duties of the
Under Secretary of Commerce for Intellectual Property and
Director of the United States Patent and Trademark Office*

Reaction Scheme 5-18 should be amended so that there is one less carbon on the radiation tag side chain of the product as shown:

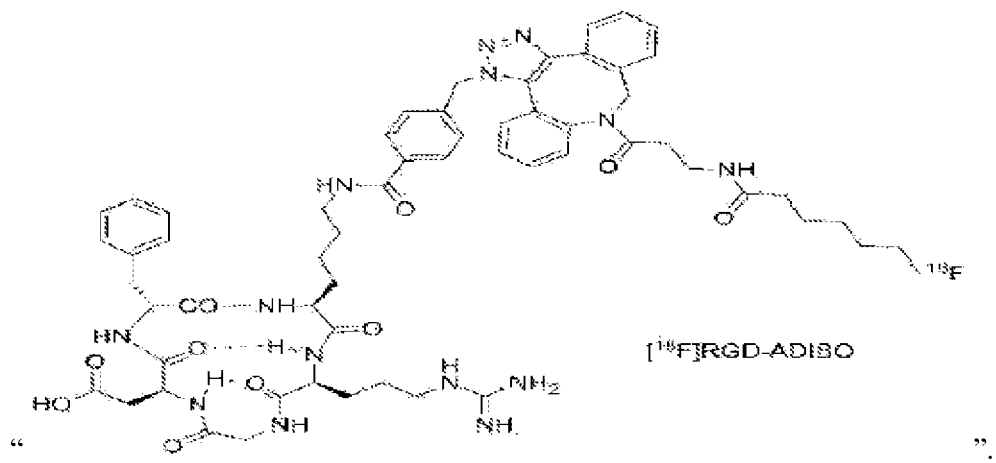

Reaction Scheme 5-20 should be amended so that Tributyltin hydride ($Bu_3Sn$) is in the place of $Su_3Sn$ as shown:

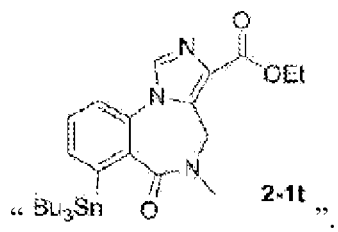

In the Claims

In Claim 1: Chemical formula 1-2 should be amended so that there is a positive charge on the Z and a negative charge on the W as shown:

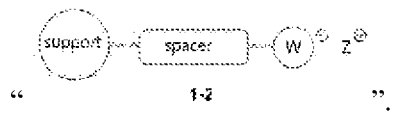

In Claim 2: The "2" in Line 49, Column 48, should be subscript as shown:
"or organic tin ($R_1R_2R_3Sn$-)....".

In Claim 3: Lines 55 through 65 should be amended to included two nitrogens, in the place of carbon, and a hydrogen as shown:

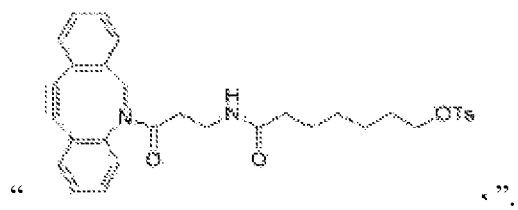

CERTIFICATE OF CORRECTION (continued)
U.S. Pat. No. 9,550,704 B2

In Claim 5: In Line 1, the number "1" should be deleted after the words "reaction solution". In Line 18, Column 52, there should be an "i" replaced with a "l" so that the solvent's name reads "3-propylcyclopentanol".

In Claim 6: There should be a positive charge on the potassium in Line 25 as shown:

"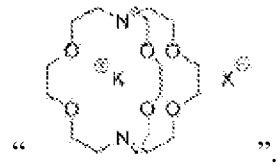".

In Claim 13: There should be a nitrogen instead of a carbon in the chemical structure as shown:

"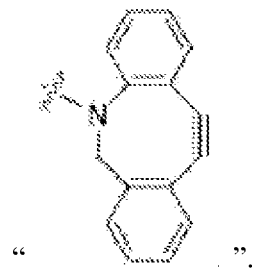".